(12) United States Patent
Miyoshi et al.

(10) Patent No.: US 10,321,809 B2
(45) Date of Patent: Jun. 18, 2019

(54) ROTARY UNIT AND INSERTION DEVICE

(71) Applicant: OLYMPUS CORPORATION, Tokyo (JP)

(72) Inventors: Hiroaki Miyoshi, Fuchu (JP); Robert Ailinger, Norwood, MA (US); James J. Frassica, Chelmsford, MA (US); Richard Andrews, Lincoln, RI (US)

(73) Assignee: OLYMPUS CORPORATION, Tokyo (JP)

( * ) Notice: Subject to any disclaimer, the term of this patent is extended or adjusted under 35 U.S.C. 154(b) by 159 days.

(21) Appl. No.: 14/568,436

(22) Filed: Dec. 12, 2014

(65) Prior Publication Data

US 2015/0164303 A1 Jun. 18, 2015

Related U.S. Application Data

(63) Continuation of application No. PCT/JP2013/066244, filed on Jun. 12, 2013.

(Continued)

(30) Foreign Application Priority Data

Jun. 13, 2012 (JP) ................ 2012-134024

(51) Int. Cl.
*A61B 1/00* (2006.01)
(52) U.S. Cl.
CPC ........ *A61B 1/0016* (2013.01); *A61B 1/00073* (2013.01); *A61B 1/00135* (2013.01); *Y10T 74/1987* (2015.01)
(58) Field of Classification Search
CPC ..... A61B 1/0016; A61B 1/01; A61B 1/00073; A61B 1/00135; Y10T 74/1987
See application file for complete search history.

(56) References Cited

U.S. PATENT DOCUMENTS

2005/0251108 A1* 11/2005 Frassica ............... A61B 1/0008
604/540
2005/0272976 A1* 12/2005 Tanaka ............... A61B 1/00073
600/114

(Continued)

FOREIGN PATENT DOCUMENTS

JP 2004-229922 A 8/2004
JP 2005-288035 A 10/2005

(Continued)

OTHER PUBLICATIONS

Extended Supplementary European Search Report dated Feb. 16, 2016 from related European Application No. 13 80 4010.0.

(Continued)

*Primary Examiner* — Alexandra L Newton
*Assistant Examiner* — Genja M Frankert
(74) *Attorney, Agent, or Firm* — Scully, Scott, Murphy & Presser, P.C.

(57) ABSTRACT

A rotary unit includes a first taper tubular portion which is contiguous to a first axial direction side of a unit main body portion and in which a first unit end of the rotary unit is positioned, an outer diameter of the first taper tubular portion becoming smaller toward the first axial direction. The rotary unit includes a first projecting portion extended on an outer peripheral portion of the first taper tubular portion with projecting toward an outer peripheral direction and wound toward a first around-axis direction as the first projecting portion extends from the first axial direction toward a second axial direction.

14 Claims, 17 Drawing Sheets

Related U.S. Application Data

(60) Provisional application No. 61/662,619, filed on Jun. 21, 2012.

(56) References Cited

U.S. PATENT DOCUMENTS

| | | | |
|---|---|---|---|
| 2009/0005645 A1* | 1/2009 | Frassica | A61B 1/0008 600/137 |
| 2010/0185179 A1* | 7/2010 | Chan | A61B 17/3478 604/508 |
| 2011/0282156 A1* | 11/2011 | Lenker | A61B 17/3439 600/208 |

FOREIGN PATENT DOCUMENTS

| | | |
|---|---|---|
| JP | 2005-323888 A | 11/2005 |
| JP | 2007-125356 A | 5/2007 |
| JP | 2007-185394 A | 7/2007 |
| JP | 2007-330811 A | 12/2007 |
| JP | 2011-520563 A | 7/2011 |
| WO | WO 2009/143077 A1 | 11/2009 |
| WO | WO 2011/030632 A1 | 3/2011 |
| WO | WO 2011/085319 A1 | 7/2011 |

OTHER PUBLICATIONS

Chinese Office Action dated Aug. 23, 2016 in related Chinese Patent Application No. 201380031587.6.

English translation of International Preliminary Report on Patentability together with the Written Opinion dated Dec. 24, 2014 received in related International Application No. PCT/JP2013/066244.

International Search Report dated Jul. 23, 2013 issued in PCT/JP2013/066244.

Office Action dated Nov. 14, 2017 in European Patent Application No. 13 804 010.0.

* cited by examiner

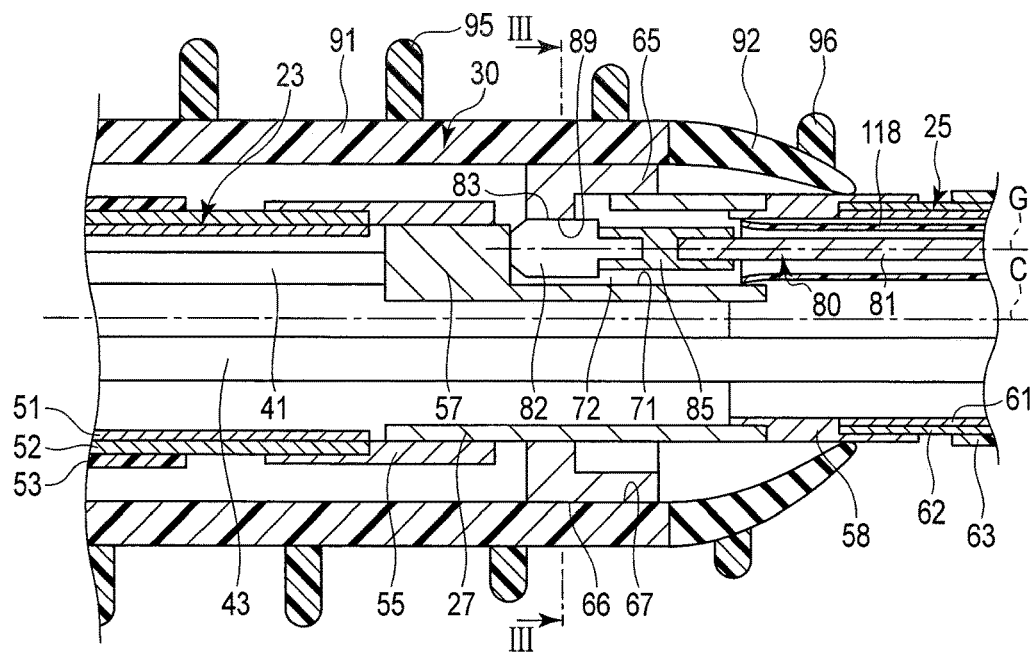
F I G. 2
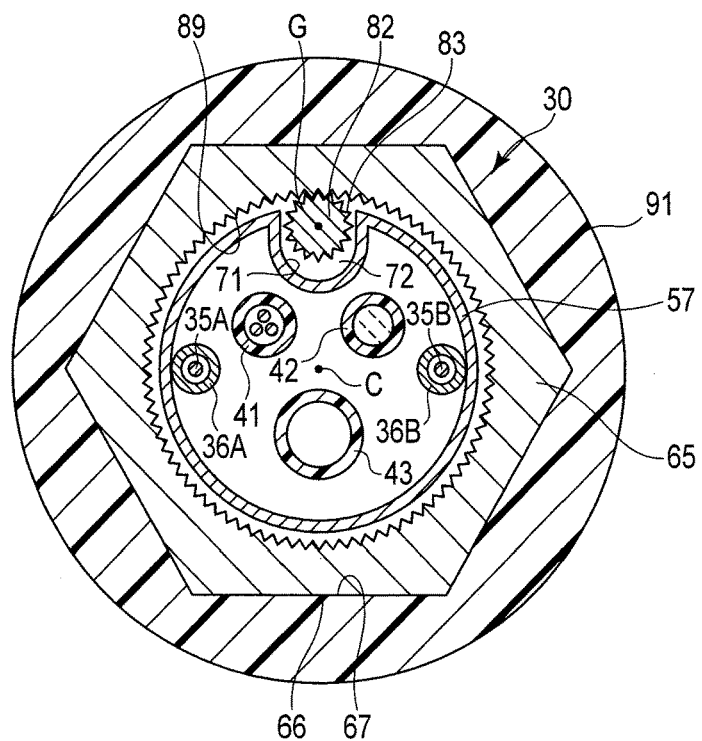
F I G. 3

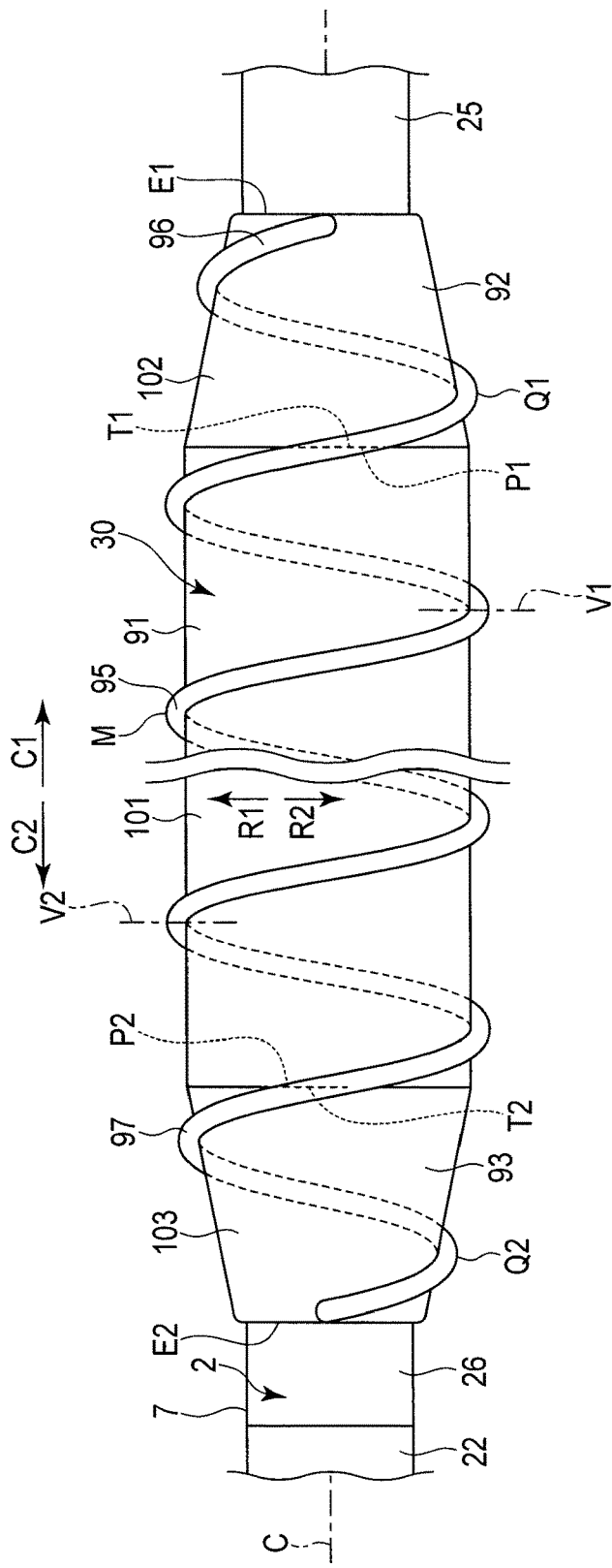
F I G. 4

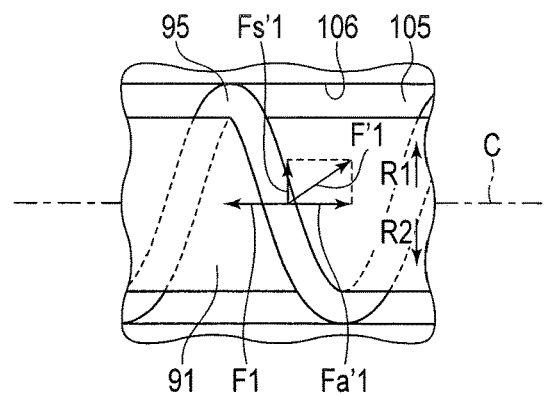
F I G. 6
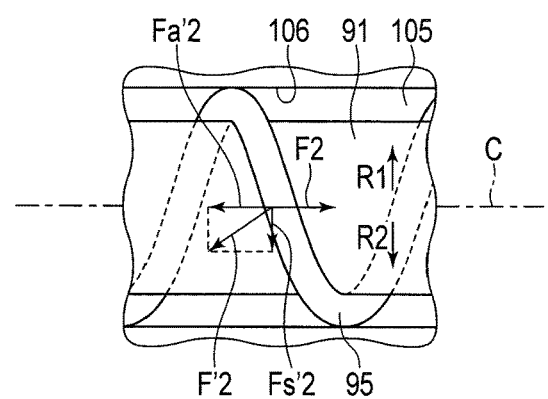
F I G. 7
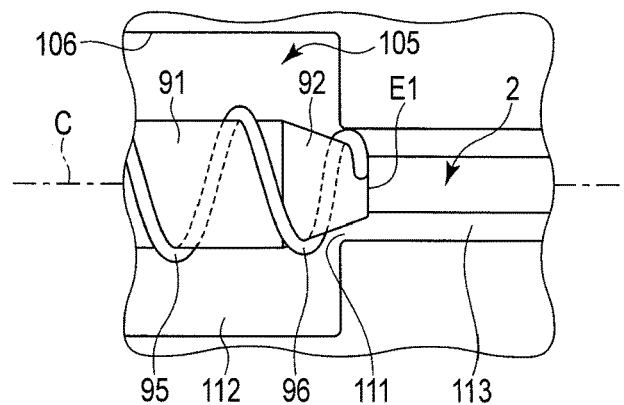
F I G. 8

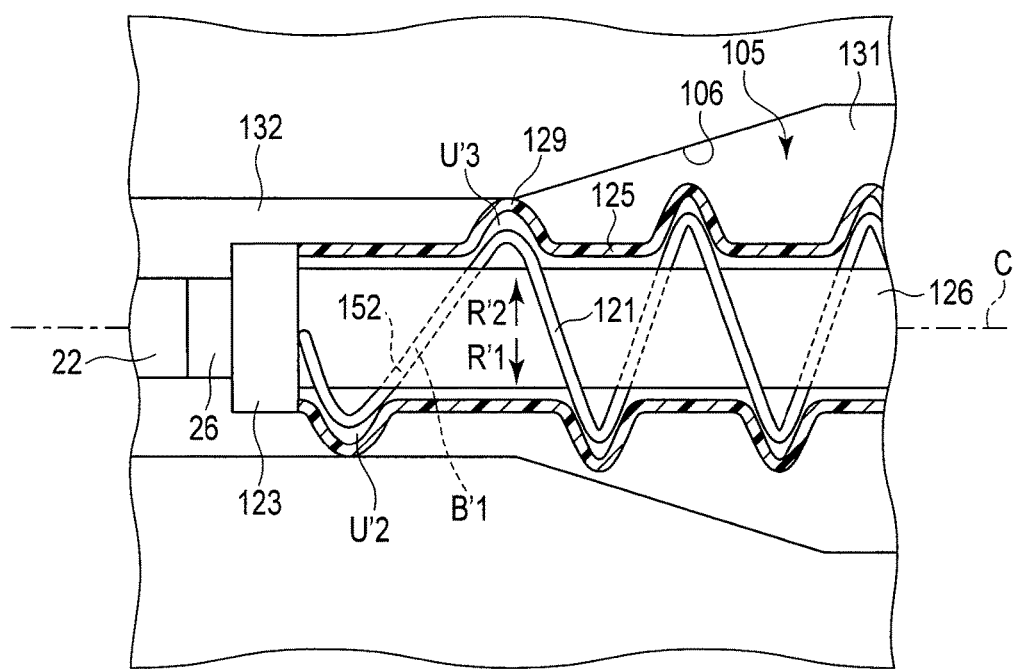
F I G. 25

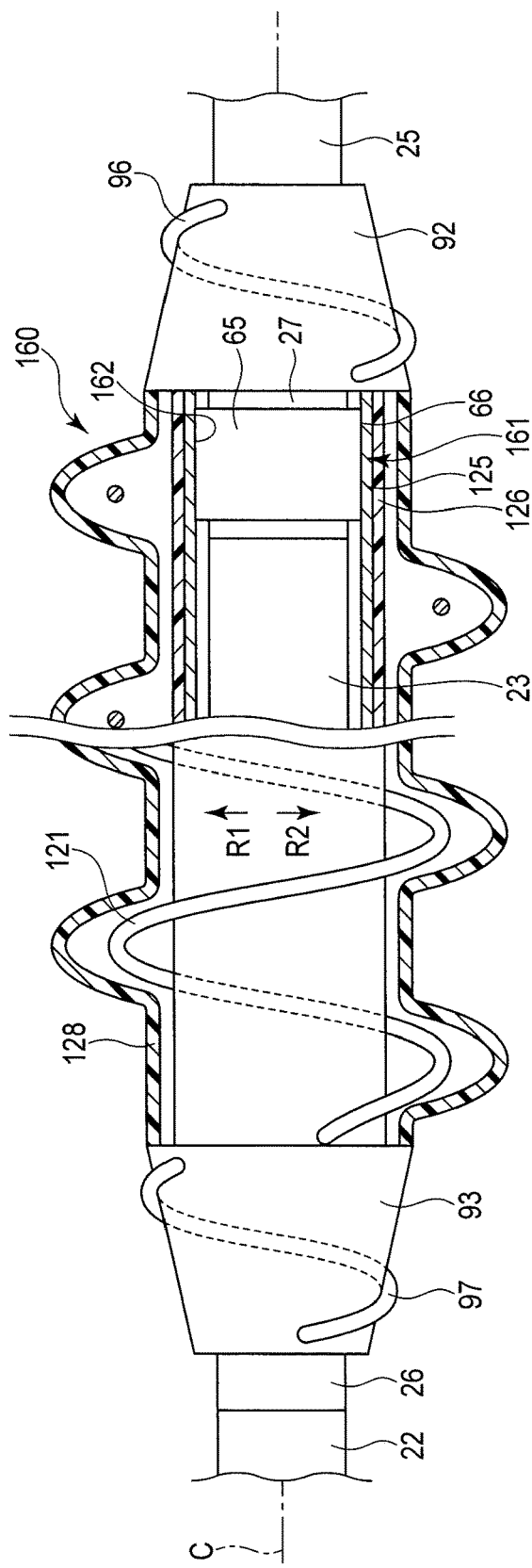
F I G. 26

ROTARY UNIT AND INSERTION DEVICE

CROSS-REFERENCE TO RELATED APPLICATIONS

This is a Continuation Application of PCT Application No. PCT/JP2013/066244, filed Jun. 12, 2013 and based upon and claiming the benefit of priority from prior Japanese Patent Application No. 2012-134024, filed Jun. 13, 2012; and prior U.S. Provisional Application No. 61/662,619, filed Jun. 21, 2012, the entire contents of both of which are incorporated herein by reference.

BACKGROUND OF THE INVENTION

1. Field of the Invention

The present invention relates to a rotary unit which is attached to an inserting section extended along a longitudinal axis so that the rotary unit is rotatable in directions around the longitudinal axis. Furthermore, it relates to an insertion device including the rotary unit.

2. Description of the Related Art

In Jpn. Pat. Appln. KOKAI Publication No. 2005-323888, an endoscope device is disclosed as an insertion device including an inserting section extended along a longitudinal axis, and a rotary unit rotatable with respect to the inserting section in directions around the longitudinal axis. The rotary unit includes a tubular unit main body portion (tubular shaped unit), a proximal-side tubular portion provided to a proximal direction side (a first axial direction side) with respect to the unit main body portion, and a distal-side tubular portion provided to a distal direction side (a second axial direction side) with respect to the unit main body portion. A proximal end (a first unit end) of the rotary unit is positioned in the proximal-side tubular portion, and a distal end (a second unit end) of the rotary unit is positioned in the distal-side tubular portion.

Furthermore, in the rotary unit, a fin portion projecting toward an outer peripheral direction is extended on an outer peripheral portion of the unit main body portion. The fin portion is wound spirally toward one (a first around-axis direction) of the directions around the longitudinal axis as the fin portion extends from the proximal direction side toward the distal direction side. In a lumen, the rotary unit rotates in one of the directions around the longitudinal axis in a state that the fin portion is in contact with a luminal paries, whereby, for example, a propelling force toward the distal direction acts on the inserting section and the rotary unit. On the other hand, the rotary unit rotates in the other (a second around-axis direction) of the directions around the longitudinal axis in the state that the fin portion is in contact with the luminal paries, whereby, for example, a propelling force toward the proximal direction acts on the inserting section and the rotary unit.

BRIEF SUMMARY OF THE INVENTION

According to one aspect of the invention, a rotary unit through which an inserting section extended along a longitudinal axis is inserted and which is attached to a base section of the inserting section in a rotatable state with respect to the inserting section in directions around the longitudinal axis, when the longitudinal axis is defined to be extended from a first axial direction toward a second axial direction that is a direction opposite to the first axial direction, the rotary unit including: a tubular unit main body portion extended along the longitudinal axis; a first taper tubular portion which is contiguous to a first axial direction side of the unit main body portion and in which a first unit end that is a first-axial-direction-side end of the rotary unit is positioned, an outer diameter of the first taper tubular portion becoming smaller toward the first axial direction; and a first projecting portion which is extended on an outer peripheral portion of the first taper tubular portion from the first unit end toward a second axial direction side in a state projecting toward an outer peripheral direction and which is wound spirally toward a first around-axis direction that is one of the directions around the longitudinal axis as the first projecting portion extends from the first axial direction toward the second axial direction, a projection diametric dimension between the longitudinal axis and a projection projecting end becoming larger from the first axial direction toward the second axial direction in the first projecting portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a sectional view schematically showing a constitution of a second relay connecting section of an inserting section according to the first embodiment;

FIG. 3 is a sectional view cut along the III-III line of FIG. 2;

FIG. 4 is a side view schematically showing a rotary unit according to the first embodiment;

FIG. 6 is a schematic view explaining a state in which the rotary unit according to the first embodiment rotates toward a first around-axis direction in a lumen;

FIG. 7 is a schematic view explaining a state in which the rotary unit according to the first embodiment rotates toward a second around-axis direction in the lumen;

FIG. 8 is a schematic view showing a state in which a unit proximal end of the rotary unit according to the first embodiment moves from a stomach to an esophagus toward a proximal direction in a cardia;

FIG. 25 is a schematic view showing a state in which the spiral fin portion is deformed from the state of FIG. 24 by an elastic force which acts in a contraction region; and FIG. 26 is a schematic view showing a rotary unit according to a fourth modification.

DETAILED DESCRIPTION OF THE INVENTION (First Embodiment)

Figure 1:
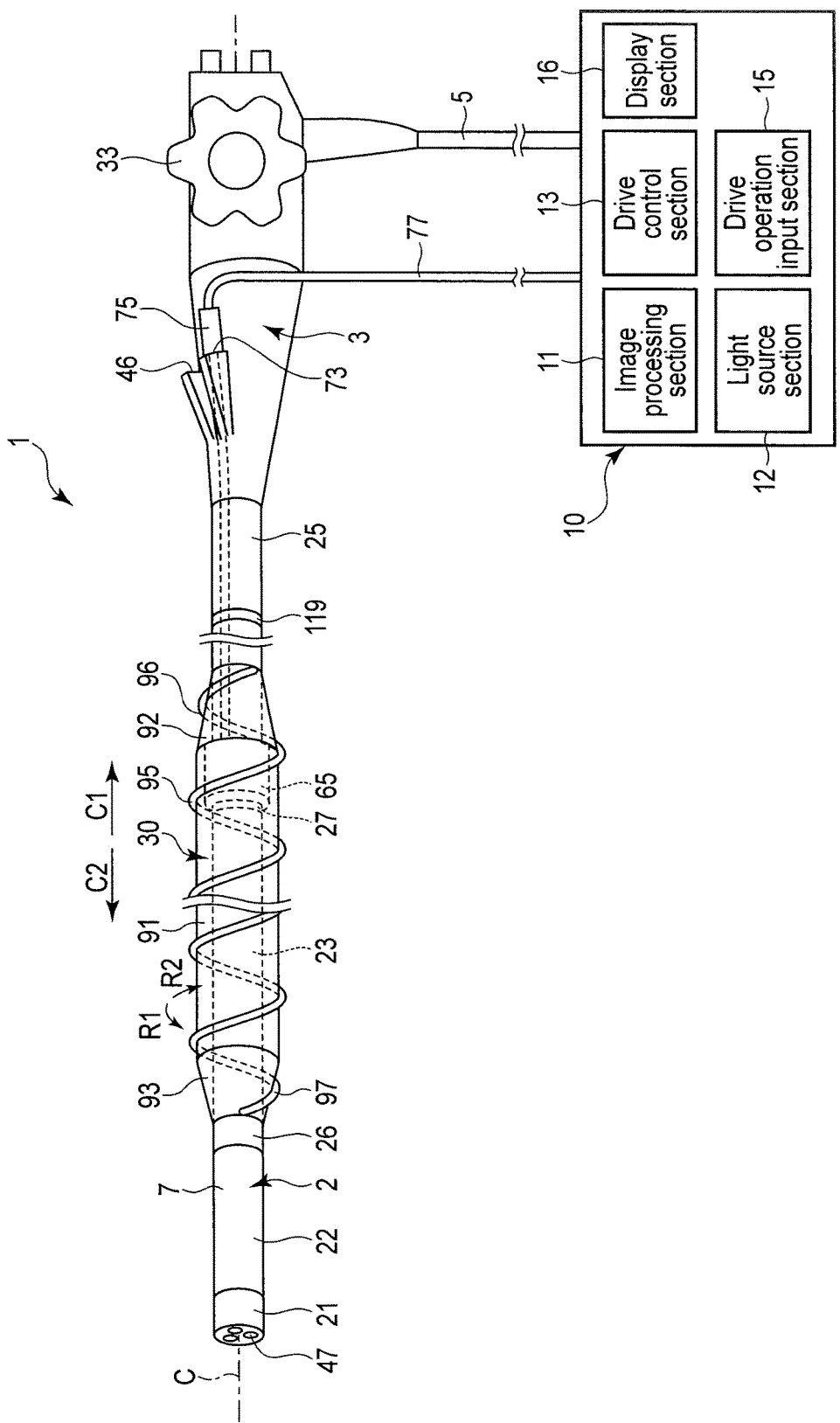
FIG. 1 is a schematic view showing an endoscope device according to a first embodiment.

A first embodiment of the present invention will be described with reference to FIG. 1 to FIG. 9. FIG. 1 is a view showing an endoscope device 1 which is an insertion device according to the first embodiment. As shown in FIG. 1, the endoscope device 1 includes an inserting section (an endoscope inserting section) 2 extended along a longitudinal axis C, and an operating section (an endoscope operating section) 3 provided to a proximal direction side with respect to the inserting section 2. The inserting section 2 is extended along the longitudinal axis C, and is configured to be inserted into a body cavity during use of the endoscope device 1. Furthermore, in the inserting section 2, an outer peripheral portion 7 is extended along the longitudinal axis C.

One end of a universal cable 5 is connected to the operating section 3. The other end of the universal cable 5 is connected to a peripheral unit 10. The peripheral unit 10 includes an image processing section 11, a light source section 12, a drive control section 13(controller), a drive operation input section 15, and a display section 16. It is to be noted that one of directions parallel to the longitudinal axis C is a proximal direction (a direction of an arrow C1 of FIG. 1), and a direction opposite to the proximal direction is a distal direction (a direction of an arrow C2 of FIG. 1). Furthermore, in the present embodiment, the proximal direction is a first axial direction, and the distal direction is a second axial direction. Therefore, the inserting section 2 is extended from the first axial direction toward the second axial direction.

The inserting section 2 includes a distal hard section 21 provided most distally, a bending section 22 provided to the proximal direction with respect to the distal hard section 21, a first flexible section 23 provided to the proximal direction side with respect to bending section 22, and a second flexible section 25 provided to the proximal direction side with respect to the first flexible section 23. The bending section 22 is connected to the first flexible tube section 23 via a first relay connecting section 26. Furthermore, the first flexible tube section 23 is connected to the second flexible tube section 25 via a second relay connecting section 27.

To an outer peripheral direction side of the inserting section 2, a rotary unit 30 is disposed. The inserting section 2 is inserted through the rotary unit 30. The rotary unit 30 is extended along the longitudinal axis C between the first relay connecting section 26 and the second relay connecting section 27. Furthermore, the rotary unit 30 is rotatable with respect to the inserting section 2 in directions around the longitudinal axis. Here, one of directions around the longitudinal axis is a first around-axis direction (a direction of an arrow R1 of FIG. 1), and a direction opposite to the first around-axis direction is a second around-axis direction (a direction of an arrow R2 of FIG. 1). In the present embodiment, a clockwise direction seen from the proximal direction side (a first axial direction side) is the first around-axis direction, and a counterclockwise direction seen from the base direction side (the first axial direction side) is the second around-axis direction.

FIG. 2 is a view showing a constitution of the second relay connecting section 27, and FIG. 3 is a sectional view cut along the III-III line of FIG. 2. As shown in FIG. 1, on the outer surface of the operating section 3, a bending operation knob 33 is disposed as a bending operation input section in which a bending operation of the bending section 22 is input. As shown in FIG. 3, inside the inserting section 2, bending wires 35A and 35B are extended along the longitudinal axis C. Inside the operating section 3, bases of the bending wires 35A and 35B are connected to a pulley (not shown) coupled to the bending operation knob 33. Distal ends of the bending wires 35A and 35B are connected to a distal portion of the bending section 22. By the bending operation in the bending operation knob 33, the bending wire 35A or 35B is pulled, whereby the bending section 22 bends.

Each of the bending wires 35A and 35B is inserted into a corresponding coil 36A or 36B. Proximal ends of the coils 36A and 36B are fixed to an inner peripheral portion of the operating section 3. Furthermore, distal ends of the coils 36A and 36B are connected to an inner peripheral portion of the first relay connecting section 26. It is to be noted that in the present embodiment, the two bending wires 35A and 35B are provided, and the bending section 22 is bendable in two directions. However, for example, four bending wires may be provided so that the bending section 22 is bendable in four directions.

As shown in FIG. 2 and FIG. 3, inside the inserting section 2, an imaging cable 41, a light guide 42 and a treatment tool channel tube 43 are extended along the longitudinal axis C. Inside the distal hard section 21 (a tip portion of the inserting section 2), an imaging element (not shown) configured to image a subject is disposed. A tip end of the imaging cable 41 is connected to the imaging element. The imaging cable 41 is extended through the inside of the inserting section 2, an inside of the operating section 3, and an inside of the universal cable 5, and a base end of the imaging cable is connected to the image processing section 11 of the peripheral unit 10. The subject image processed by the image processing section 11 is displayed on the display section 16. Furthermore, the light guide 42 is extended through the inside of the inserting section 2, the inside of the operating section 3, and the inside of the universal cable 5, and a proximal end of the light guide is connected to the light source section 12 of the peripheral unit 10. Light emitted from the light source section 12 is guided by the light guide 42, and applied onto the subject from the distal portion (the tip hard section 21) of the inserting section 2.

As shown in FIG. 1, on the outer surface of the operating section 3, there is provided a treatment tool inserting portion 46 into which a treatment tool such as forceps is inserted. The treatment tool channel tube 43 passes through the inside of the inserting section 2 and the inside of the operating section 3, and a base end of the tube is connected to the treatment tool inserting portion 46. The treatment tool inserted from the treatment tool inserting portion 46 passes through an inside of the treatment tool channel tube 43 to project from an opening 47 of the distal hard section 21 toward the distal direction. Furthermore, a treatment by the treatment tool is performed in a state where the treatment tool is projected from the opening 47 of the tip hard section 21.

As shown in FIG. 2, in the first flexible tube section 23, a first helical tube (a first flex) 51 made of a metal is provided. An outer peripheral side of the first helical tube 51 is covered with a first flexible reticular tube (a first flexible blade) 52 made of a metal. An outer peripheral side of the first flexible reticular tube 52 is covered with a first flexible outer cover 53 made of a resin. A proximal portion of the first helical tube 51 and a proximal portion of the first flexible reticular tube 52 are fitted into a distal portion of a relay member 55. The second relay connecting section 27 includes a base member 57 made of a metal. A base portion of the relay member 55 is fitted into the base member 57. In such a manner as described above, the first flexible tube section 23 is coupled to the second relay connecting section 27.

In the second flexible tube section 25, a second helical tube (a second flex) 61 made of a metal is provided. An outer peripheral side of the second helical tube 61 is covered with a second flexible reticular tube (a second flexible blade) 62 made of a metal. An outer peripheral side of the second flexible reticular tube 62 is covered with a second flexible outer cover 63 made of a resin. A distal portion of the second helical tube 61 and a distal portion of the second flexible reticular tube 62 are fitted into a relay member 58. The relay member 58 is fitted into the base member 57. In such a manner as described above, the second flexible tube section 25 is coupled to the second relay connecting section 27.

A rotary tubular member 65 is attached to the second relay connecting section 27 of the inserting section 2 in a state that the inserting section 2 is inserted through the rotary tubular member. The rotary tubular member 65 is rotatable with respect to the inserting section 2 in the directions around the longitudinal axis. Furthermore, movement of the rotary tubular member 65 with respect to the inserting section 2 in the directions parallel to the longitudinal axis C is regulated. On an outer peripheral side of the rotary tubular member 65, the rotary unit 30 is positioned.

As shown in FIG. 3, the rotary tubular member 65 is provided with a polygonal outer peripheral portion 66 in which a shape of a cross section perpendicular to the longitudinal axis C is substantially hexagonal. Furthermore, the rotary unit 30 is provided with a polygonal inner peripheral portion 67 in which a cross section perpendicular to the longitudinal axis C passing the rotary tubular member 65 is formed into a substantially hexagonal shape corresponding to the polygonal outer peripheral portion 66 of the rotary tubular member 65. Consequently, the polygonal inner peripheral portion 67 of the rotary unit 30 comes in close contact with the polygonal outer peripheral portion 66 of the rotary tubular member 65, and the rotary unit 30 is attached to the outer peripheral direction side of the rotary tubular member 65. In consequence, the rotary unit 30 is rotatable with respect to the inserting section 2 integrally with the rotary tubular member 65 in the directions around the longitudinal axis. That is, the base member 57 is a base section to which the rotary unit 30 is attached via the rotary tubular member 65 in a state that the rotary unit is rotatable in the periaxis directions of the longitudinal axis.

It is to be noted that in the present embodiment, each of the polygonal outer peripheral portion 66 and the polygonal inner peripheral portion 67 is formed into the substantially hexagonal shape, but it is not limited to this example. For example, the polygonal outer peripheral portion 66 may be formed into a substantially octagonal shape, and the polygonal inner peripheral portion 67 may be formed into a substantially octagonal shape corresponding to the polygonal outer peripheral portion 66.

As shown in FIG. 2 and FIG. 3, in the base member 57 (the base section), a gear arrangement cavity 72 is defined by a cavity defining portion 71. An outside of the inserting section 2 communicates with an inside thereof via the gear arrangement space 72.

As shown in FIG. 1, on the outer surface of the operating section 3, a member inserting portion 73 is provided. Furthermore, a motor 75(generator) which is a drive member is attached to the member inserting portion 73. One end of a motor cable 77 is connected to the motor 75. The other end of the motor cable 77 is connected to the drive control section 13 of the peripheral unit 10.

As shown in FIG. 2 and FIG. 3, in the second flexible section 25 and the gear arrangement cavity 72 of the inserting section 2, a drive unit 80 is provided. Furthermore, inside the second flexible tube section 25, a member channel tube 118 is extended. The member inserting portion 73 is coupled to a proximal portion of the base member 57 by the member channel tube 118. The drive unit 80 is inserted through the member channel tube 118. The drive unit 80 is driven so as to be rotatable around a drive axis G. The drive unit 80 includes a drive shaft 81 which is a linear member extended along the drive axis G, and a drive gear 82 provided to a tip direction side with respect to the drive shaft 81. Over the all-round of the drive gear 82 in directions around the drive axis, a gear potion 83 is provided. The drive shaft 81 is coupled to the drive gear 82 via a connecting member 85. Furthermore, a proximal end of the drive shaft 81 is connected to the motor 75.

The motor 75 is driven by the operation in the drive operation input section 15, whereby the drive shaft 81 and the drive gear 82 rotate toward one of the directions around the drive axis. In consequence, the gear portion 83 moves toward one of directions around the drive axis. That is, when the motor 75 is driven, a drive force is transmitted to the gear portion 83 via the drive shaft 81, whereby the drive unit 80 is driven. The drive control section 13 (controller) receives the operation in the drive operation input section 15 and control the motor to adjust the drive force to rotate the drive shaft 81.

An inner peripheral portion of the rotary tubular member 65 is provided with an inner peripheral gear portion 89 which engages with the gear portion 83 of the drive gear 82. The inner peripheral gear portion 89 is provided over the whole periphery of the rotary tubular member 65 in the directions around the longitudinal axis. Consequently, when the gear portion 83 rotates around the drive axis G, the rotary tubular member 65 rotates in one of the directions around the longitudinal axis. When the rotary tubular member 65 rotates, a rotary drive force is transmitted to the polygonal inner peripheral portion 67 of the rotary unit 30, whereby the rotary unit 30 rotates with respect to the inserting section 2 toward one of the directions around the longitudinal axis. That is, the polygonal inner peripheral portion 67 is a drive force receiving portion which receives the rotary drive force when the drive unit 80 is driven, thereby rotating the rotary unit 30.

Figure 5:
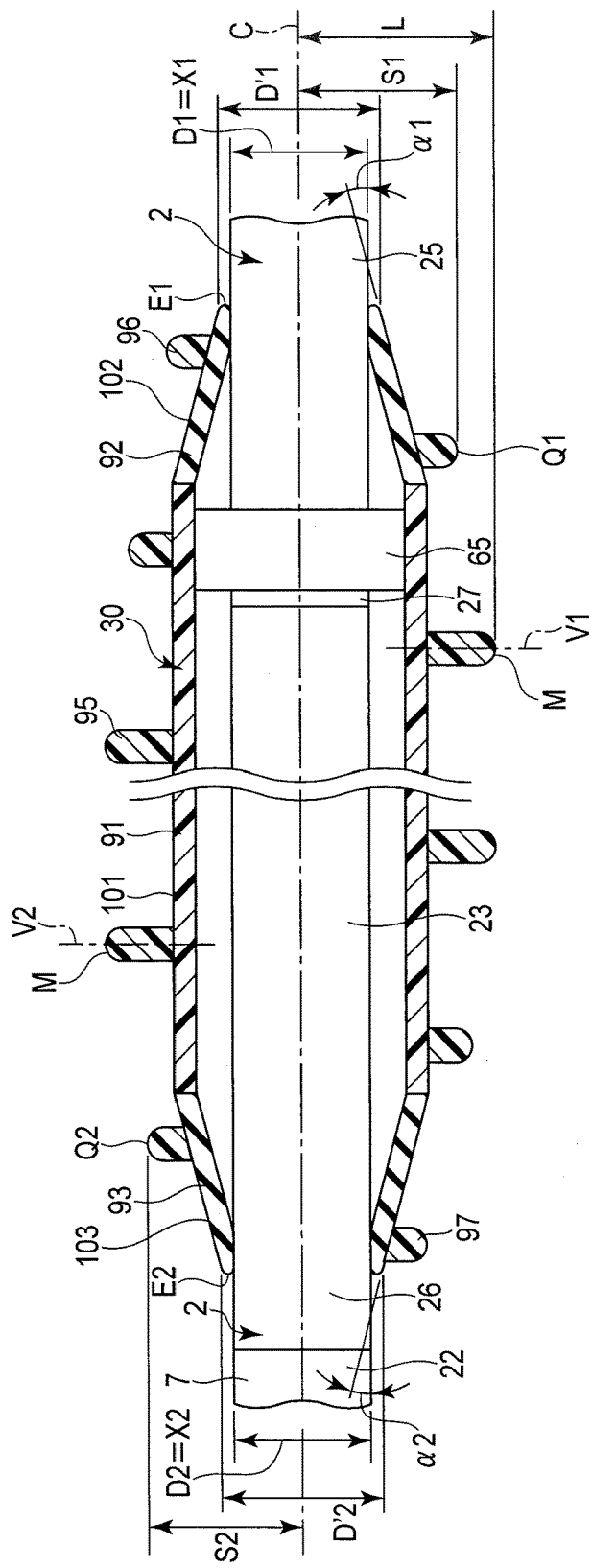
FIG. 5 is a sectional view schematically showing the rotary unit according to the first embodiment.

FIG. 4 and FIG. 5 are views showing a constitution of the rotary unit 30. As shown in FIG. 4 and FIG. 5, the rotary unit 30 includes a unit main body portion 91 extended along the longitudinal axis C. The unit main body portion 91 is formed into a tubular shape, and an outer diameter thereof is substantially constant from a proximal end to a distal end. Furthermore, the unit main body portion has a clearance between the outer peripheral portion 7 of the inserting section 2 (the first flexible section 23) and an inner peripheral portion of the unit main body portion 91. The polygonal inner peripheral portion 67 of the rotary unit 30 is disposed in a proximal portion of the unit main body portion 91.

In the rotary unit 30, a proximal-side taper tubular portion 92, which is a first taper tubular portion, is contiguous to the proximal direction side (the first axial direction side) of the unit main body portion 91. An outer diameter of the proximal-side taper tubular portion 92 decreases toward the proximal direction side. Furthermore, a proximal end of the base-side taper tubular portion 92 is a unit proximal end E1 which is the proximal end (the first-axial-direction-side end) of the rotary unit 30. That is, in the proximal-side taper tubular portion 92, the unit proximal end E1 which is a first unit end is positioned.

Furthermore, in the rotary unit 30, a distal-side taper tubular portion 93, which is a second taper tubular portion, is contiguous to a distal direction side (a second axial direction side) of the unit main body portion 91. An outer diameter of the distal-side taper tubular portion 93 decreases toward the distal direction side. Furthermore, the distal end of the tip-side taper tubular portion 93 is a unit distal end E2 which is the distal end (the second-axial-direction-side end) of the rotary unit 30. That is, in the distal-side taper tubular portion 93, the unit distal end E2 which is a second unit end is positioned.

In the rotary unit 30, a fin portion 95 projected toward an outer peripheral direction is extended on an outer peripheral portion 101 of the unit main body portion 91. The fin portion 95 is spirally wound toward the first around-axis direction as the fin portion extends from the proximal direction (the first axial direction) toward the distal direction (the second axial direction). The fin portion 95 is extended between a fin extending proximal end (a first fin extending end) P1 which is the proximal-direction-side end thereof and a fin extending distal end (a second fin extending end) P2 which is the distal-direction-side end thereof. Furthermore, an outer-peripheral-side end of the fin portion 95 is a fin projecting end M.

Furthermore, in the rotary unit 30, a proximal-side projecting portion 96 which is a first projecting portion is extended on an outer peripheral portion 102 of the proximal-side taper tubular portion 92 in a state that the proximal-side projecting portion projects toward the outer peripheral direction. The proximal-side projecting portion 96 is wound toward the first around-axis direction as the proximal-side projecting portion extends from the base direction (the first axial direction) toward the tip direction (the second axial direction). The proximal-side projecting portion 96 is extended up to a proximal-side projection extending distal end (a first projection extending end) T1 which is the distal-direction-side end thereof. Furthermore, an outer-peripheral-side end of the proximal-side projecting portion 96 is a proximal-side projection projecting end (a first projection projecting end) Q1.

The proximal-side projection extending distal end T1 of the proximal-side projecting portion 96 is contiguous to the fin extending proximal end P1 of the fin portion 95. In the base-side projecting portion 96, a proximal-side projection diametric dimension (a first projection diametric dimension) S1 between the longitudinal axis C and the proximal-side projection projecting end Q1 becomes larger from the proximal direction (the first axial direction) toward the distal direction (the second axial direction). Therefore, at the proximal-side projection extending distal end T1, the proximal-side projection diametric dimension S1 is maximum.

At the fin extending proximal end P1, a fin diametric dimension L between the longitudinal axis C and the fin projecting end M of the fin portion 95 is the same as the proximal-side projection diametric dimension S1 at the proximal-side projection extending distal end T1. Furthermore, at a proximal-side reference position (a first reference position) V1 located to the distal direction side (the second axial direction side) with respect to the fin extending proximal end P1, the fin diametric dimension L is maximum. The fin diametric dimension L becomes larger from the proximal direction (the first axial direction) toward the distal direction (the second axial direction) between the fin extending proximal end P1 and the proximal-side reference position V1. Therefore, also in the outer peripheral portion 101 of the unit main body section 91 in which an outer diameter is substantially constant, the fin diametric dimension L becomes larger from the fin extending base end P1 toward the base-side reference position V1.

Furthermore, in the rotary unit 30, a distal-side projecting portion 97 which is a second projecting portion projected toward the outer peripheral direction is extended on an outer peripheral portion 103 of the distal-side taper tubular portion 93. The tip-side projecting portion 97 is wound toward the first around-axis direction as the projecting portion extends from the proximal direction (the first axial direction) toward the distal direction (the second axial direction). The distal-side projecting portion 97 is extended up to a distal-side projection extending proximal end (a second projection extending end) T2 which is the proximal-direction-side end thereof. Furthermore, an outer-peripheral-side end of the distal-side projecting portion 97 is a distal-side projection projecting end (a second projection projecting end) Q2.

The distal-side projection extending proximal end T2 of the distal-side projecting portion 97 is contiguous to the fin extending distal end P2 of the fin portion 95. In the distal-side projecting portion 97, a distal-side projection diametric dimension (a second projection diametric dimension) S2 between the longitudinal axis C and the distal-side projection projecting end Q2 becomes larger from the distal direction (the second axial direction) toward the proximal direction (the first axial direction). Therefore, at the distal-side projection extending proximal end T2, the distal-side projection diametric dimension S2 is maximum.

At the fin extending distal end P2, the fin diametric dimension L is the same as the distal-side projection diametric dimension S2 at the distal-side projection extending proximal end T2. Furthermore, at a distal-side reference position (a second reference position) V2 located to the proximal direction side (the first axial direction side) with respect to the fin extending distal end P2, the fin diametric dimension L is maximum. The fin diametric dimension L becomes larger from the tip direction (the second axial direction) toward the base direction (the first axial direction) between the fin extending distal end P2 and the distal-side reference position V2. Therefore, also in the outer peripheral portion 101 of the unit main body section 91 in which the outer diameter is substantially constant, the fin diametric dimension L becomes larger from the fin extending tip end P2 toward the tip-side reference position V2.

The distal-side reference position V2 is located to the distal direction side (the second axial direction side) with respect to the proximal-side reference position V1. In a region between the proximal-side reference position V1 and the distal-side reference position V2, the fin diametric dimension L is constant and maximum.

At the unit proximal end (the first unit end) E1 of the rotary unit 30, an inner diameter D1 of the proximal-side taper tubular portion 92 is about the same as an outer diameter X1 of the inserting section 2. Therefore, at the unit proximal end E1, the inner peripheral portion of the proximal-side taper tubular portion 92 comes in contact with the outer peripheral portion 7 of the inserting section 2 without any clearance. However, at the unit base end E1, the base-side taper tubular portion 92 is movable with respect to the inserting section 2 in the directions around the longitudinal axis. Furthermore, at the unit proximal end E1, an outer diameter D'1 of the proximal-side taper tubular portion 92 is at a ratio of 1 to 1.26 with respect to the outer diameter X1 of the inserting section 2. Furthermore, at the unit proximal end E1, an acute angle α1 between the outer peripheral portion 102 of the proximal-side taper tubular portion 92 and the outer peripheral portion 7 of the inserting section 2 is from 5° to 20°.

According to such a constitution as described above, at the unit proximal end (the first unit end) E1 of the rotary unit 30, the outer diameter D'1 of the rotary unit 30 is not excessively larger than the outer diameter X1 of the inserting section 2. Consequently, at the unit base end E1 of the rotary unit 30, a stepped portion is unlikely to be formed, and the outer peripheral portion 102 of the proximal-side taper tubular portion 92 is contiguous to the outer peripheral portion 7 of the inserting section 2. Furthermore, the acute angle α1 is from 5° to 20°, and hence in a part to the distal direction side of the unit proximal end E1, the outer diameter of the proximal-side taper tubular portion 92 of the rotary unit 30 moderately increases.

At the unit distal end (the second unit end) E2 of the rotary unit 30, an inner diameter D2 of the distal-side taper tubular portion 93 is about the same as an outer diameter X2 of the inserting section 2. Consequently, at the unit tip end E2, an inner peripheral portion of the tip-side taper tubular portion 93 comes in contact with the outer peripheral portion 7 of the inserting section 2 without any clearance. However, at the unit distal end E2, the distal-side taper tubular portion 93 is movable with respect to the inserting section 2 in the directions around the longitudinal axis. Furthermore, at the unit distal end E2, an outer diameter D'2 of the distal-side taper tubular portion 93 is at a ratio of 1 to 1.26 with respect to the outer diameter X2 of the inserting section 2. Furthermore, at the unit distal end E2, an acute angle α2 between the outer peripheral portion 103 of the distal-side taper tubular portion 93 and the outer peripheral portion 7 of the inserting section 2 is from 5° to 20°.

According to such a constitution as described above, at the unit distal end (the second unit end) E2 of the rotary unit 30, the outer diameter D'2 of the rotary unit 30 is not excessively larger than the outer diameter X2 of the inserting section 2. Consequently, at the unit tip end E2 of the rotary unit 30, a stepped portion is unlikely to be formed, and the outer peripheral portion 103 of the tip-side taper tubular portion 93 is contiguous to the outer peripheral portion 7 of the inserting section 2. Furthermore, the acute angle α2 is from 5° to 20°, and hence in a part to the proximal direction side of the unit distal end E2, the outer diameter of the distal-side taper tubular portion 93 of the rotary unit 30 moderately increases.

Next, an function of the endoscope device 1 and the rotary unit 30 of the present embodiment will be described. During use of the endoscope device 1, the inserting section 2, to which the rotary tubular member 65 and the rotary unit 30 are attached, is inserted into a lumen. Then, by the operation in the drive operation input section 15, the motor 75 is driven. Consequently, the drive unit 80 is driven, whereby the drive unit 80 rotates in one of the directions around the drive axis. When the gear portion 83 of the drive unit 80 rotates around the drive axis G, the rotary drive force is transmitted to the inner peripheral gear portion 89, whereby the rotary tubular member 65 and the rotary unit 30 integrally rotate with respect to the inserting section 2 in one of the directions around the longitudinal axis.

FIG. 6 is an explanatory view of a state in which the rotary unit 30 rotates toward the first around-axis direction (a direction of an arrow R1 of FIG. 6) in a lumen 105. When the rotary unit 30 is rotated toward the first around-axis direction in a state that the fin portion 95 of the rotary unit 30 is in contact with a luminal paries 106, a pressing force F'1 acts from the fin portion 95 onto the luminal paries 106. The pressing force F'1 acts toward a direction which is tilted with respect to the first around-axis direction toward the proximal direction side and which is perpendicular to an extending direction of the fin portion 95. The pressing force F'1 is decomposed into a circumferential force component Fs'1 in the first around-axis direction and an axial force component Fa'1 in the proximal direction (the first axial direction). As a reaction of the axial force component Fa'1 of the pressing force F'1, a propelling force F1 toward the distal direction (the second axial direction) acts from the luminal paries 106 to the inserting section 2 and the rotary unit 30. The propelling force F1 enhances inserting properties of the inserting section 2 into the lumen 105.

It is to be noted that when the rotary unit 30 is similarly rotated in the first periaxis direction also in a state that the proximal-side projecting portion 96 is in contact with the luminal paries 106, the propelling force F1 in the distal direction acts on the inserting section 2 and the rotary unit 30. Furthermore, when the rotary unit 30 is similarly rotated in the first around-axis direction also in a state that the distal-side projecting portion 97 is in contact with the luminal paries 106, the propelling force F1 toward the distal direction acts on the inserting section 2 and the rotary unit 30.

FIG. 7 is an explanatory view of a state in which the rotary unit 30 rotates toward the second around-axis direction (a direction of an arrow R2 of FIG. 7) in the lumen 105. When the rotary unit 30 is rotated toward the second around-axis direction in the state that the fin portion 95 of the rotary unit 30 is in contact with the luminal paries 106, a pressing force F'2 acts from the fin portion 95 onto the luminal paries 106. The pressing force F'2 acts in a direction which is tilted with respect to the second around-axis direction toward the distal direction side and which is perpendicular to the extending direction of the fin portion 95. The pressing force F'2 is decomposed into a circumferential force component Fs'2 in the second periaxis direction and an axial force component Fa'2 in the distal direction (the second axial direction). As a reaction of the axial force component Fa'2 of the pressing force F'2, a propelling force F2 toward the proximal direction (the first axial direction) acts from the luminal paries 106 to the inserting section 2 and the rotary unit 30. The propelling force F2 enhances removing properties of the inserting section 2 from the lumen 105.

It is to be noted that when the rotary unit 30 is similarly rotated in the second around-axis direction also in the state that the proximal-side projecting portion 96 is in contact with the luminal paries 106, the propelling force F2 in the base direction acts on the inserting section 2 and the rotary unit 30. Furthermore, when the rotary unit 30 is similarly rotated toward the second around-axis direction also in the state that the distal-side projecting portion 97 is in contact with the luminal paries 106, the propelling force F2 toward the proximal direction acts on the inserting section 2 and the rotary unit 30.

Furthermore, in the lumen 105, there is a part where a sectional area rapidly changes. Examples of the part where the sectional area of the lumen 105 rapidly changes include a cardia between a stomach having a large sectional area and an esophagus having a small sectional area, and a pylorus between the stomach having the large sectional area and a duodenum having a small sectional area. When the inserting section 2 and the rotary unit 30 move in directions parallel to the longitudinal axis C in the lumen 105, the unit proximal end E1 or the unit distal end E2 of the rotary unit 30 sometimes moves from a region of a large sectional area to a region of a small sectional area in the portion where the sectional area rapidly changes.

FIG. 8 is a view showing that the unit proximal end E1 of the rotary unit 30 moves from a stomach 112 to an esophagus 113 toward the proximal direction (the first axial direction) in a cardia 111. As shown in FIG. 8, when the inserting section 2 and the rotary unit 30 are removed in a state that the inserting section 2 and the rotary unit 30 have been inserted from the mouth to the stomach 112, the unit base end E1 of the rotary unit 30 passes the cardia 111. Here, the outer diameter of the proximal-side taper tubular portion 92 becomes smaller toward the proximal direction side, and hence the base-side taper tubular portion 92 is easily moved from the stomach 112 to the esophagus 113 having a small sectional area.

Furthermore, as described above, at the unit proximal end E1 of the rotary unit 30, a stepped portion is unlikely to be formed, and the outer peripheral portion 102 of the proximal-side taper tubular portion 92 is contiguous to the outer peripheral portion 7 of the inserting section 2. Furthermore, in the part to the distal direction side with respect to the unit proximal end E1, the outer diameter of the proximal-side taper tubular portion 92 of the rotary unit 30 moderately increases. Consequently, in the movement of the unit proximal end E1 from the stomach 112 to the esophagus 113 in the cardia 111, the unit base end E1 does not easily abut on the luminal paries 106, and the drawing out properties of the inserting section 2 are enhanced.

Furthermore, the outer peripheral portion 102 of the proximal-side taper tubular portion 92 is provided with the proximal-side projecting portion 96. Therefore, when the unit proximal end E1 provided in the proximal-side taper tubular portion 92 moves to the esophagus 113, the proximal-side projecting portion 96 comes in contact with the luminal paries 106 in the esophagus 113. When the rotary unit 30 is rotated toward the second around-axis direction in the state that the base-side projecting portion 96 is in contact with the luminal paries 106, the propelling force F2 toward the proximal direction acts on the inserting section 2 and the rotary unit 30 as described above. Consequently, when the rotary unit 30 moves from the stomach 112 having a large sectional area to the esophagus 113 having a small sectional area in the cardia 111 where the sectional area rapidly changes, the removing properties of the inserting section 2 are acquired. That is, when the unit proximal end E1 of the rotary unit 30 moves through the cardia 111, moving properties of the inserting section 2 toward the proximal direction (the first axial direction), which is one of the directions parallel to the longitudinal axis C, are acquired.

Furthermore, in the proximal-side projecting portion 96, the proximal-side projection diametric dimension S1 between the longitudinal axis C and the proximal-side projection projecting end Q1 becomes larger from the proximal direction (the first axial direction) toward the distal direction (the second axial direction). Consequently, when the unit proximal end E1 of the rotary unit 30 moves to the esophagus 113 in the cardia 111, the proximal-side projecting portion 96 easily comes in contact with the luminal paries 106 in the esophagus 113. In consequence, when the unit base end E1 of the rotary unit 30 moves through the cardia 111, the removing properties of the inserting section 2 further enhance.

Furthermore, at the fin extending proximal end P1, the fin diametric dimension L is the same as the proximal-side projection diametric dimension S1 at the proximal-side projection extending distal end T1. Furthermore, at the proximal-side reference position V1, the fin diametric dimension L is maximum. Furthermore, the fin diametric dimension L becomes larger from the base direction (the first axial direction) toward the tip direction (the second axial direction) between the fin extending base end P1 and the base-side reference position V1. According to the above-mentioned constitution, the proximal-side taper tubular portion 92 moves to the esophagus 113, and then in the cardia 111, the unit main body portion 91 easily moves to the esophagus 113. Furthermore, when the unit main body portion 91 moves to the esophagus 113 in the cardia 111, the fin portion 95 easily comes in contact with the luminal paries 106 in the esophagus 113. Consequently, when the rotary unit 30 moves through the cardia 111, the removing properties of the inserting section 2 are further enhanced. Furthermore, as shown in FIG. 1, an index 119 may be provided on the outer surface of the second flexible tube section 25. In this case, the index 119 is disposed at a position which is away from the proximal end position (the unit proximal end E1) of the proximal-side taper tubular portion 92 by as much as an average length from the mouth to the cardia 111. When the proximal-side taper tubular portion 92 moves to the esophagus 113 beyond the cardia 111, the index 119 moves from the mouth to the outside of the body toward the proximal direction. Therefore, an operator can visually confirm, from the index 119, that the unit main body portion 91 moves toward the esophagus 113 without being disturbed at the cardia 111.

It is to be noted that the cardia 111 has been described as an example of a part where the sectional area rapidly changes, in the case where the unit proximal end E1 of the rotary unit 30 moves through the part, but it is not limited to this example. Another example of the portion where the sectional area rapidly changes in the lumen 105 is a part between a rectum having a large sectional area and an anus having a small sectional area. When the inserting section 2 and the rotary unit 30 are removed in a state that the inserting section 2 and the rotary unit 30 have been inserted from the anus to the rectum, the unit proximal end E1 of the rotary unit 30 passes the part between the rectum and the anus. Also in this case, the moving properties of the inserting section 2 toward the proximal direction (the first axial direction) are acquired in the same manner as in the case where the unit base end E1 moves through the cardia 111.

Figure 9:
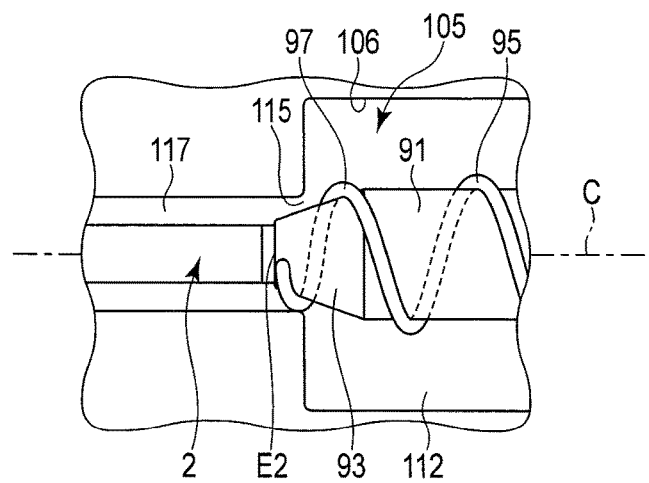
FIG. 9 is a schematic view showing a state in which a unit distal end of the rotary unit according to the first embodiment moves from the stomach to a duodenum toward a distal direction in a pylorus.

FIG. 9 is a view showing that the unit distal end E2 of the rotary unit 30 moves from the stomach 112 to a duodenum 117 toward the distal direction (the second axial direction) in a pylorus 115. As shown in FIG. 9, when the inserting section 2 and the rotary unit 30 are inserted from the mouth to the duodenum 117, the unit distal end E2 of the rotary unit 30 passes the pylorus 115. Here, the outer diameter of the distal-side taper tubular portion 93 becomes smaller toward the distal direction side, so that the tip-side taper tubular portion 93 can easily be moved from the stomach 112 to the duodenum 117 having a small sectional area.

Furthermore, as described above, at the unit tip end E2 of the rotary unit 30, a stepped portion is unlikely to be formed, and the outer peripheral portion 103 of the distal-side taper tubular portion 93 is contiguous to the outer peripheral portion 7 of the inserting section 2. Furthermore, in the part to the proximal direction side with respect to the unit distal end E2, the outer diameter of the distal-side taper tubular portion 93 of the rotary unit 30 moderately increases. Therefore, in the movement of the unit distal end E2 from the stomach 112 to the duodenum 117 in the pylorus 115, the unit tip end E2 does not easily abut on the luminal paries 106, and inserting properties of the inserting section 2 are enhanced.

Furthermore, the outer peripheral portion 103 of the distal-side taper tubular portion 93 is provided with the distal-side projecting portion 97. Consequently, when the unit distal end E2 provided in the distal-side taper tubular portion 93 moves to the duodenum 117, the distal-side projecting portion 97 comes in contact with the luminal paries 106 in the duodenum 117. When the rotary unit 30 is rotated toward the first around-axis direction in the state that the distal-side projecting portion 97 is in contact with the luminal paries 106, the propelling force F1 toward the distal direction acts on the inserting section 2 and the rotary unit 30 as described above. Consequently, when the rotary unit 30 moves from the stomach 112 having a large sectional area to the duodenum 117 having a small sectional area in the pylorus 115 where the sectional area rapidly changes, the inserting properties of the inserting section 2 are acquired. That is, when the unit tip end E2 of the rotary unit 30 moves through the pylorus 115, the moving properties of the inserting section 2 toward the distal direction (the second axial direction), which is the other of the directions parallel to the longitudinal axis C, are acquired.

Furthermore, in the distal-side projecting portion 97, the distal-side projection diametric dimension S2 between the longitudinal axis C and the distal-side projection projecting end Q2 becomes larger from the distal direction (the second axial direction) toward the proximal direction (the first axial direction). Consequently, when the unit tip end E2 of the rotary unit 30 moves to the duodenum 117 in the pylorus 115, the tip-side projecting portion 97 easily comes in contact with the luminal paries 106 in the duodenum 117. In consequence, when the unit distal end E2 of the rotary unit 30 moves through the pylorus 115, the inserting properties of the inserting section 2 are further enhanced.

Furthermore, at the fin extending distal end P2, the fin diametric dimension L is the same as the distal-side projection diametric dimension S2 at the distal-side projection extending proximal end T2. Furthermore, at the distal-side reference position V2, the fin diametric dimension L is maximum. Furthermore, the fin diametric dimension L becomes larger from the tip direction (the second axial direction) toward the base direction (the first axial direction) between the fin extending tip end P2 and the tip-side reference position V2. According to the above-mentioned constitution, the distal-side taper tubular portion 93 moves to the duodenum 117, and then in the pylorus 115, the unit main body portion 91 easily moves to the duodenum 117. Furthermore, when the unit main body portion 91 moves to the duodenum 117 in the pylorus 115, the fin portion 95 easily comes in contact with the luminal paries 106 in the duodenum 117. In consequence, when the rotary unit 30 moves through the pylorus 115, the inserting properties of the inserting section 2 are further enhanced.

It is to be noted that the pylorus 115 has been described as the example of the part where the sectional area rapidly changes, in the case where the unit distal end E2 of the rotary unit 30 moves through the part, but it is not limited to this example. An example of the portion where the sectional area rapidly changes in the lumen 105 is an ileocecal valve between a large intestine having a large sectional area and a small intestine having a small sectional area. When the inserting section 2 and the rotary unit 30 are inserted from the anus into the small intestine, the unit distal end E2 of the rotary unit 30 passes the ileocecal valve. Also in this case, the moving properties of the inserting section 2 toward the distal direction (the second axial direction) are acquired in the same manner as in the case where the unit tip end E2 moves through the pylorus 115.

Thus, in the endoscope device 1 of the above constitution, the following effects are produced. That is, in the endoscope device 1, the outer peripheral portion 102 of the proximal-side taper tubular portion 92 is provided with the proximal-side projecting portion 96. Therefore, in the part where the sectional area of the lumen 105 rapidly changes, when the unit proximal end (the first unit end) E1 of the rotary unit 30 moves from the region of the large sectional area to the region of the small sectional area, the proximal-side projecting portion 96 comes in contact with the luminal paries 106 in the region of the small sectional area. When the rotary unit 30 is rotated toward the second around-axis direction in the state that the proximal-side projecting portion 96 is in contact with the luminal paries 106, the propelling force F2 in the proximal direction acts on the inserting section 2 and the rotary unit 30 as described above. In consequence, when the rotary unit 30 moves from the region of the large sectional area to the region of the small sectional area in the part where the sectional area rapidly changes, it is possible to acquire the moving properties of the inserting section 2 toward the proximal direction (the first axial direction) parallel to the longitudinal axis C.

Furthermore, in the endoscope device 1, the outer peripheral portion 103 of the distal-side taper tubular portion 93 is provided with the distal-side projecting portion 97. Consequently, when the unit distal end (the second unit end) E2 of the rotary unit 30 moves from the region of the large sectional area to the region of the small sectional area in the part where the sectional area of the lumen 105 rapidly changes, the distal-side projecting portion 97 comes in contact with the luminal paries 106 in the region of the small sectional area. When the rotary unit 30 is rotated toward the first around-axis direction in the state that the tip-side projecting portion 97 is in contact with the luminal paries 106, the propelling force F1 in the distal direction acts on the inserting section 2 and the rotary unit 30 as described above. Consequently, when the rotary unit 30 moves from the region of the large sectional area to the region of the small sectional area in the portion where the sectional area rapidly changes, it is possible to acquire the moving properties of the inserting section 2 in the distal direction (the second axial direction) parallel to the longitudinal axis C.

(Modifications of First Embodiment)

Figure 10:
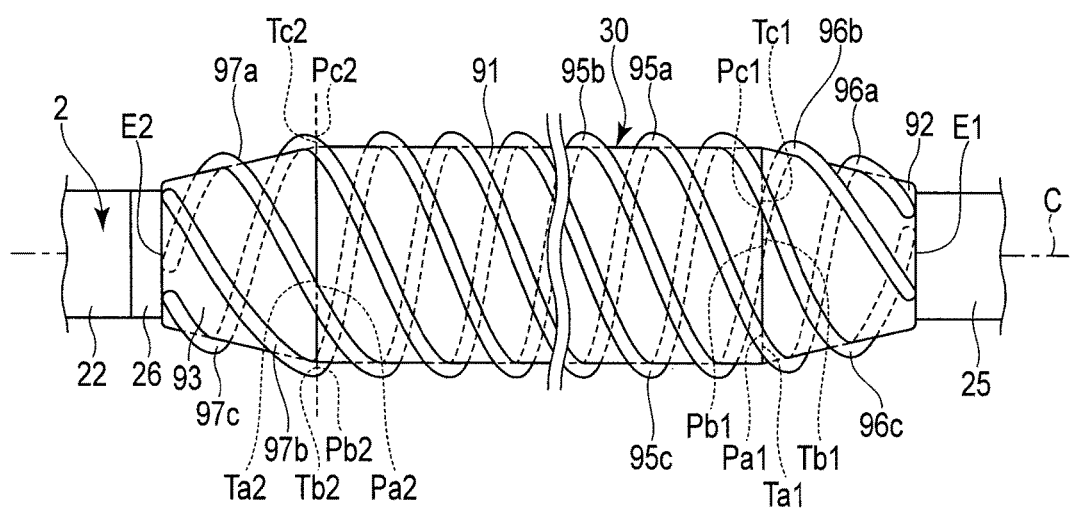
FIG. 10 is a side view schematically showing a rotary unit according to a first modification.

It is to be noted that in the first embodiment, only one fin portion 95, only one proximal-side projecting portion 96 and only one distal-side projecting portion 97 are provide, but it is not limited to this example. For example, as a first modification shown in FIG. 10, there may be provided fin portions 95a to 95c, proximal-side projecting portions 96a to 96c, and distal-side projecting portions 97a to 97c. Also in the present modification, the fin portions 95a to 95c, the base-side projecting portions 96a to 96c and the tip-side projecting portions 97a to 97c are wound toward a first around-axis direction as the portions extend from a proximal direction (a first axial direction) toward a distal direction (a second axial direction). The fin portions 95a to 95c are disposed away from one another in directions around a longitudinal axis. Furthermore, the proximal-side projecting portions 96a to 96c are disposed away from one another in the directions around the longitudinal axis. Similarly, the distal-side projecting portions 97a to 97c are disposed away from one another in the directions around the longitudinal axis.

In the present modification, a proximal-side projection extending distal end Ta1 which is a first projection extending end of the proximal-side projecting portion 96a is contiguous to a fin extending proximal end Pa1 which is a first fin extending end of the fin portion 95a. Similarly, a proximal-side projection extending distal end (a first projection extending end) Tb1 of the proximal-side projecting portion 96b is contiguous to a fin extending proximal end (a first fin extending end) Pb1 of the fin portion 95b, and a proximal-side projection extending distal end (a first projection extending end) Tc1 of the proximal-side projecting portion 96c is contiguous to a fin extending proximal end (a first fin extending end) Pc1 of the fin portion 95c. Furthermore, a distal-side projection extending proximal end Ta2 which is a second projection extending end of the distal-side projecting portion 97a is contiguous to a fin extending distal end Pa2 which is a second fin extending end of the fin portion 95a. Similarly, a distal-side projection extending proximal end (a second projection extending end) Tb2 of the distal-side projecting portion 97b is contiguous to a fin extending distal end (a second fin extending end) Pb2 of the fin portion 95b, and a distal-side projection extending proximal end (a second projection extending end) Tc2 of the distal-side projecting portion 97c is contiguous to a fin extending distal end (a second fin extending end) Pc2 of the fin portion 95c.

In the present modification, the base-side projecting portions 96a to 96c are provided. Consequently, when a rotary unit 30 is rotated toward a second around-axis direction in a state that the proximal-side projecting portions 96a to 96c are in contact with a luminal paries 106, a propelling force F2 toward the proximal direction, which acts on an inserting section 2 and the rotary unit 30, increases. Therefore, moving properties of the inserting section 2 toward the proximal direction (the first axial direction) are enhanced. Furthermore, in the present modification, the distal-side projecting portions 97a to 97c are provided. When the rotary unit 30 is rotated toward the first around-axis direction in a state that the tip-side projecting portions 97a to 97c are in contact with the luminal paries 106, a propelling force F1 toward the distal direction, which acts on the inserting section 2 and the rotary unit 30, increases. Therefore, the moving properties of the inserting section 2 toward the distal direction (the second axial direction) are enhanced.

Figure 11:
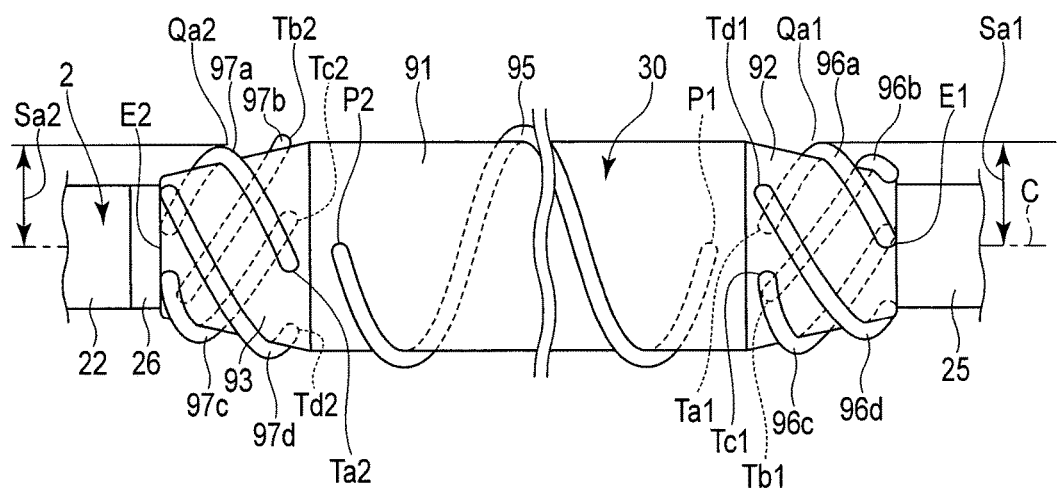
FIG. 11 is a side view schematically showing a rotary unit according to a second modification.

Furthermore, in the first embodiment, the proximal-side projection extending distal end (the first projection extending end) T1 of the proximal-side projecting portion 96 is contiguous to the fin extending proximal end (the first fin extending end) P1 of the fin portion 95, and the distal-side projection extending proximal end (the second projection extending end) T2 of the distal-side projecting portion 97 is contiguous to the fin extending distal end (the second fin extending end) P2 of the fin portion 95, but it is not limited to this example. For example, as a second modification shown in FIG. 11, proximal-side projecting portions 96a to 96d are provided, and proximal-side projection extending distal ends (first projection extending ends) Ta1 to Td1 of the respective proximal-side projecting portions 96a to 96d do not have to be contiguous to a fin extending proximal end (a first fin extending end) P1 of a fin portion 95. Furthermore, in the present modification, distal-side projecting portions 97a to 97d are provided, and distal-side projection extending proximal ends (second projection extending ends) Ta2 to Td2 of the respective distal-side projecting portions 97a to 97d are not contiguous to a fin extending distal end (a second fin extending end) P2 of the fin portion 95.

Also in the present modification, the fin portion 95, the base-side projecting portions 96a to 96d and the tip-side projecting portions 97a to 97d are wound toward a first around-axis direction as the portions extend from a proximal direction (a first axial direction) toward a distal direction (a second axial direction). The proximal-side projecting portions 96a to 96d are disposed away from one another in directions around a longitudinal axis. Similarly, the distal-side projecting portions 97a to 97d are disposed away from one another in the directions around the longitudinal axis.

In the proximal-side projecting portion 96a, a proximal-side projection diametric dimension (a first projection diametric dimension) Sa1 between a longitudinal axis C and a proximal-side projection projecting end (a first projection projecting end) Qa1 becomes larger from the base direction (the first axial direction) toward the tip direction (the second axial direction). Also, as to each of the proximal-side projecting portions 96b to 96d, each of proximal-side projection diametric dimensions Sb1 to Sd1 between the longitudinal axis C and each of proximal-side projection projecting ends Qb1 to Qd1 becomes larger from the proximal direction (the first axial direction) toward the distal direction (the second axial direction) in the same manner as in the proximal-side projecting portion 96a. Furthermore, in the distal-side projecting portion 97a, a distal-side projection diametric dimension (a second projection diametric dimension) Sa2 between the longitudinal axis C and a distal-side projection projecting end (a second projection projecting end) Qa2 becomes larger from the tip direction (the second axial direction) toward the base direction (the first axial direction). Also, as to each of the distal-side projecting portions 97b to 97d, each of distal-side projection diametric dimensions Sb2 to Sd2 between the longitudinal axis C and each of distal-side projection projecting ends Qb2 to Qd2 becomes larger from the distal direction (the second axial direction) toward the proximal direction (the first axial direction) in the same manner as in the distal-side projecting portion 97a.

In the present modification, the proximal-side projecting portions 96a to 96d are provided. Therefore, when a rotary unit 30 is rotated in a second around-axis direction in a state that the base-side projecting portions 96a to 96d are in contact with a luminal paries 106, a propelling force F2 toward the proximal direction, which acts on the inserting section 2 and the rotary unit 30, increases. Therefore, moving properties of the inserting section 2 toward the proximal direction (the first axial direction) are enhanced. Furthermore, in the present modification, the distal-side projecting portions 97a to 97d are provided. Consequently, when the rotary unit 30 is rotated in the first around-axis direction in a state that the tip-side projecting portions 97a to 97d are in contact with the luminal paries 106, a propelling force F1 toward the distal direction, which acts on the inserting section 2 and the rotary unit 30, increases. Therefore, the moving properties of the inserting section 2 toward the distal direction (the second axial direction) are enhanced.

Furthermore, in each of the proximal-side projecting portions 96a to 96d of the present modification, each of the proximal-side projection diametric dimensions Sa1 to Sd1 between the longitudinal axis C and each of the proximal-side projection projecting ends Qa1 to Qd1 becomes larger from the base direction (the first axial direction) toward the tip direction (the second axial direction). Consequently, when a unit proximal end E1 of the rotary unit 30 moves to a region of a small sectional area at a part where a sectional area rapidly changes, for example, a cardia 111 or the like in a lumen 105, the proximal-side projecting portions 96a to 96d easily come in contact with the luminal paries 106 in the region of the small sectional area. In consequence, when the unit base end E1 of the rotary unit 30 moves through the part where the sectional area rapidly changes, the moving properties (removing properties) of the inserting section 2 toward the proximal direction (the first axial direction) are further enhanced.

Furthermore, in each of the distal-side projecting portions 97a to 97d of the present modification, each of the distal-side projection diametric dimensions Sa2 to Sd2 between the longitudinal axis C and each of the distal-side projection projecting ends Qa2 to Qd2 becomes larger from the tip direction (the second axial direction) toward the base direction (the first axial direction). Consequently, when a unit distal end E2 of the rotary unit 30 moves to the region of the small sectional area at the part where the sectional area rapidly changes, for example, a pylorus 115 or the like in the lumen 105, the tip-side projecting portions 97a to 97d easily come in contact with the luminal paries 106 in the region of the small sectional area. In consequence, when the unit tip end E2 of the rotary unit 30 moves through the part where the sectional area rapidly changes, the moving properties (inserting properties) of the inserting section 2 toward the distal direction (the second axial direction) are further enhanced.

Figure 12:
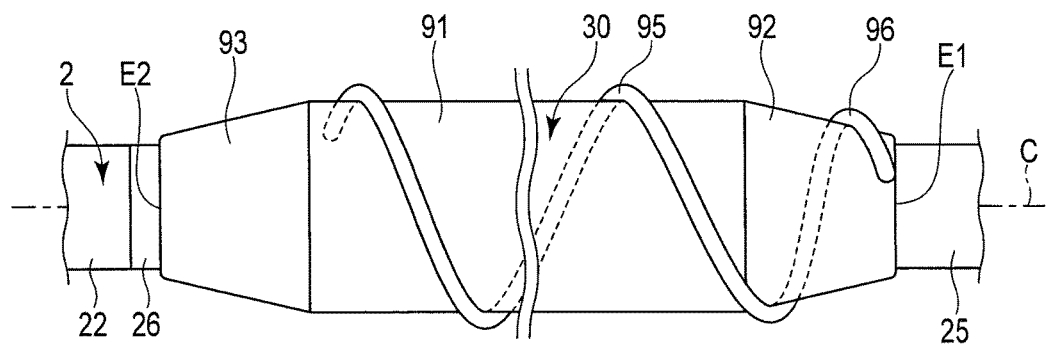
FIG. 12 is a side view schematically showing a rotary unit according to a third modification.

Furthermore, in the first embodiment, both of the Proximal-side projecting portion 96 and the distal-side projecting portion 97 are provided, but it is not limited to this example. For example, as a third modification shown in FIG. 12, a proximal-side projecting portion 96 is only provided, and a distal-side projecting portion 97 does not have to be provided. Also in the present modification, a fin portion 95 and the base-side projecting portion 96 are wound toward a first around-axis direction as the portions extend from a proximal direction (a first axial direction) toward a distal direction (a second axial direction). Furthermore, as an unshown modification, a distal-side projecting portion 97 is only provided, and a proximal-side projecting portion 96 does not have to be provided.

Furthermore, it has been described in the first embodiment that the proximal direction (the direction of the arrow C1 of FIG. 1) is the first axial direction and that the distal direction (the direction of the arrow C2 of FIG. 1) is the second axial direction, but it is not limited to this example. For example, the distal direction may be the first axial direction, and the proximal direction may be the second axial direction. In this case, a clockwise direction (a direction of an arrow R2 of FIG. 1) seen from a distal direction side (a first axial direction side) is a first around-axis direction, and a counterclockwise direction (a direction of an arrow R1 of FIG. 1) seen from the distal direction side (the first axial direction side) is a second around-axis direction. Furthermore, a distal-side taper tubular portion 93 is a first taper tubular portion, and a proximal-side taper tubular portion 92 is a second taper tubular portion. Furthermore, a unit distal end E2 is a first unit end, and a unit proximal end E1 is a second unit end.

In such a definition as described above, a fin portion 95, a proximal-side projecting portion 96 and a distal-side projecting portion 97 are wound toward the first around-axis direction as the portions extend from the tip direction (the first axial direction) toward the base direction (the second axial direction). Furthermore, the distal-side projecting portion 97 is a first projecting portion, and the proximal-side projecting portion is a second projecting portion. Therefore, a distal-side projection extending proximal end T2 of the distal-side projecting portion 97 is a first projection extending end, and a fin extending distal end P2 of the fin portion 95 is a first fin extending end. Furthermore, a distal-side projection projecting end Q2 is a first projection projecting end, and a distal-side projection diametric dimension S2 is a first projection diametric dimension. Similarly, a proximal-side projection extending distal end T1 of the proximal-side projecting portion 96 is a second projection extending end, and a fin extending proximal end P1 of the fin portion 95 is a second fin extending end. Furthermore, a proximal-side projection projecting end Q1 is a second projection projecting end, and a proximal-side projection diametric dimension S1 is a second projection diametric dimension. Furthermore, a distal-side reference position V2 is a first reference position, and a proximal-side reference position V1 is a second reference position.

(Reference Examples)

Furthermore, an endoscope device 1 according to a first reference example will be described with reference to FIG. 13 to FIG. 19. In the present reference example, in place of the rotary unit 30 of the first embodiment, a rotary unit 120 is attached to a base member (a base section) 57 via a rotary tubular member 65. The rotary unit 120 is extended along a longitudinal axis C between a first relay connecting section 26 and a second relay connecting section 27.

Figure 13:
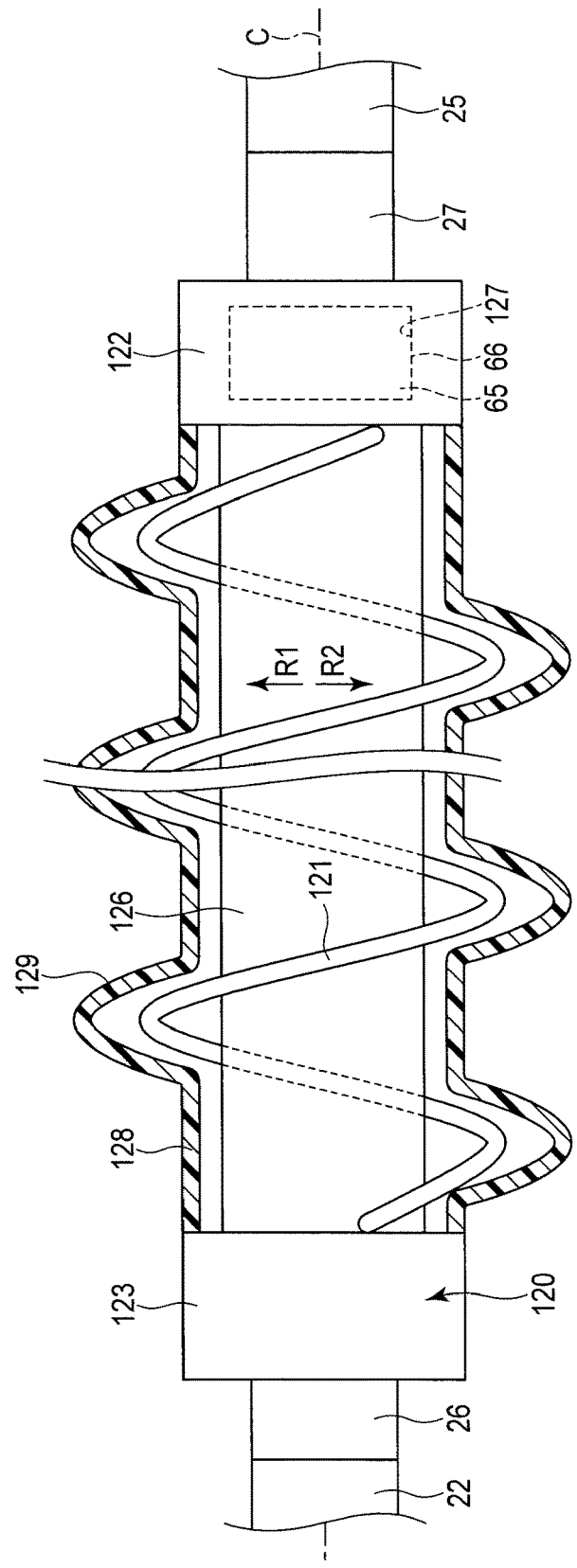
FIG. 13 is a side view schematically showing a rotary unit according to a first reference example, and a cover member only is shown in a cross section.
Figure 14:
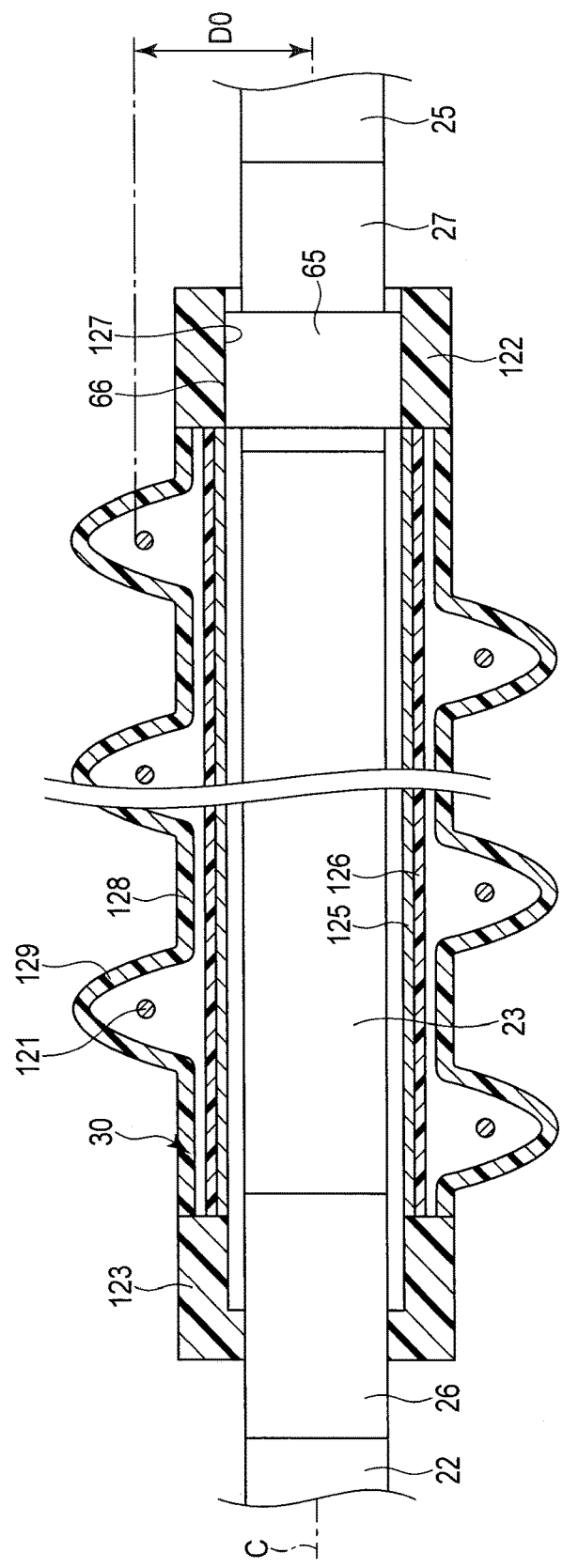
FIG. 14 is a sectional view schematically showing the rotary unit according to the first reference example.

FIG. 13 and FIG. 14 are views showing a constitution of the rotary unit 120. As shown in FIG. 13 and FIG. 14, the rotary unit (tubular shaped unit) 120 includes a spiral fin portion 121 spirally extended about the longitudinal axis C. The spiral fin portion 121 is positioned toward a first around-axis direction (a direction of an arrow R1 of FIG. 13) side from a proximal direction (a first axial direction) toward a distal direction (a second axial direction). The spiral fin portion 121 is a spring member which is expandable and contractible along the longitudinal axis C, and is made of nitinol, hardened stainless steel or the like. In a state that a pressing force toward an inner peripheral direction does not act on the rotary unit 120, the spiral fin portion 121 is in a neutral state. In the neutral state, a fin diametric dimension between the longitudinal axis C and the spiral fin portion 121 is a reference fin diametric dimension D0. The fin diametric dimension, a diameter of the spring member, is varied by an amount of twisting.

A proximal end (a first-axial-direction-side end) of the spiral fin portion 121 is connected to a tubular proximal-side connecting member 122 which is a first connecting member. An inner peripheral portion of the proximal-side connecting member 122 is provided with a polygonal inner peripheral portion 127 of a constitution similar to the polygonal inner peripheral portion 67 of the first embodiment. Therefore, the polygonal inner peripheral portion 127 which is a drive force receiving portion is provided to the proximal direction (first axial direction) side with respect to the spiral fin portion 121. The polygonal inner peripheral portion 127 of the base-side connecting member 122 comes in close contact with a polygonal outer peripheral portion 66 of the rotary tubular member 65, whereby the rotary unit 120 is attached to the rotary tubular member 65.

A distal end (a second-axial-direction-side end) of the spiral fin portion 121 is connected to a tubular distal-side connecting member 123 which is a second connecting member. The distal-side connecting member 123 is movable with respect to an inserting section 2 along the longitudinal axis C. Therefore, the tip-side connecting member 123 moves along the longitudinal axis C in accordance with the expansion and contraction of the spiral fin portion 121.

Furthermore, in the rotary unit 120, a corrugate tube 125 which is a tube member and a jacket 126 are provided to an inner peripheral direction side of the spiral fin portion 121. The jacket 126 covers an outer peripheral direction side of the corrugate tube 125. On an outer peripheral portion of the jacket 126, the spiral fin portion 121 is extended. The corrugate tube 125 and the jacket 126 are extended along the longitudinal axis C between the proximal-side connecting member 122 and the distal-side connecting member 123. Furthermore, the corrugate tube 125 and the jacket 126 are expandable and contractible along the longitudinal axis C in accordance with the movement of the distal-side connecting member 123 along the longitudinal axis C. That is, the corrugate tube 125 and the jacket 126 are expandable and contractible along the longitudinal axis C in accordance with the expansion and contraction of the spiral fin portion 121.

Furthermore, in the rotary unit 120, an outer peripheral direction side of the spiral fin portion 121 is covered with a cover member 128. The cover member 128 is an elastic member made of a material having high expansion and contraction properties, for example, latex, silicone or the like. On an outer peripheral portion of the cover member 128, the cover member 128 is partially and spirally projected along the spring, a projecting portion 129 projecting toward an outer peripheral direction is spirally extended about the longitudinal axis C. An outer peripheral side of the spiral fin portion 121 is covered with the projecting portion 129. The cover member 128 is elastically deformed in accordance with the expansion and contraction of the spiral fin portion 121 along the longitudinal axis C and a change of the fin diametric dimension between the longitudinal axis C and the spiral fin portion 121. Here, in a state that no pressing force acts on the rotary unit 120 toward the inner peripheral direction, the spiral fin portion 121 is held in the neutral state by the cover member 128.

Next, a function of the endoscope device 1 of the present reference example will be described. During use of the endoscope device 1, a motor 75 is driven in a state that the inserting section 2 to which the rotary tubular member 65 and the rotary unit 120 are attached is inserted into a lumen. Consequently, the rotary tubular member 65 rotates with respect to the inserting section 2 in the same manner as in the first embodiment. In consequence, a rotary drive force is transmitted from the rotary tubular member 65 to the polygonal inner peripheral portion 127 which is the drive force receiving portion, and the rotary tubular member 65 and the rotary unit 120 integrally rotate with respect to the inserting section 2 in one of directions around a longitudinal axis.

When the rotary unit 120 is rotated toward the first around-axis direction in a state that the projecting portion 129 of the cover member 128 of the rotary unit 120 is in contact with a luminal paries 106, a pressing force F'1 acts from the spiral fin portion 121 onto the luminal paries 106 via the projecting portion 129 in the same manner as in the rotary unit 30 of the first embodiment. Furthermore, as a reaction to an axial force component Fa'1 of the pressing force F'1, a propelling force F1 toward the distal direction (the second axial direction) acts from the luminal paries 106 to the inserting section 2 and the rotary unit 120 (see FIG. 6 of the first embodiment). Consequently, the propelling force F1 enhances inserting properties of the inserting section 2 into a lumen 105 also in the present reference example, similarly to the first embodiment.

Furthermore, when the rotary unit 120 is rotated toward a second around-axis direction in the state that the projecting portion 129 of the cover member 128 of the rotary unit 120 is in contact with the luminal paries 106, a pressing force F'2 acts from the spiral fin portion 121 onto the luminal paries 106 via the projecting portion 129 in the same manner as in the rotary unit 30 of the first embodiment. Furthermore, as a reaction to an axial force component Fa'2 of the pressing force F'2, a propelling force F2 toward the proximal direction (the first axial direction) acts from the luminal paries 106 to the inserting section 2 and the rotary unit 120 (see FIG. 7 of the first embodiment). Consequently, the propelling force F2 enhances removing properties of the inserting section 2 from the lumen 105 also in the present reference example similarly to the first embodiment.

Furthermore, in the lumen 105, there is a part where a sectional area gradually changes. For example, in a part between a duodenum and a small intestine, the sectional area gradually decreases from the duodenum toward the small intestine. Furthermore, in a portion between a cecum and a sigmoid colon in a large intestine, the sectional area gradually decreases from the cecum toward the sigmoid colon. During movement of the inserting section 2 and the rotary unit 120 in directions parallel to the longitudinal axis C in the lumen 105, the rotary unit 120 sometimes moves toward a direction toward which the sectional area decreases in the part where the sectional area gradually changes.

Figure 15:
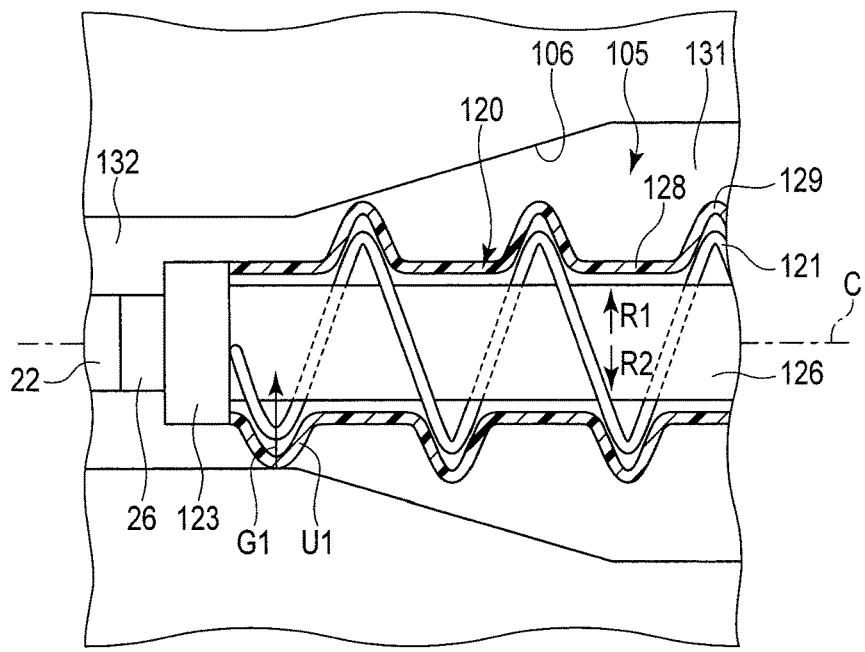
FIG. 15 is a schematic view showing a state in which the rotary unit according to the first reference example moves in a lumen from a duodenum toward a small intestine when a spiral fin portion is in a neutral state.

FIG. 15 is a view showing a state in which the rotary unit 120 moves in the lumen 105 from a duodenum 131 toward a small intestine 132 when the spiral fin portion 121 is in the neutral state. As shown in FIG. 15, when the inserting section 2 and the rotary unit 120 are inserted from a mouth up to the small intestine 132, the rotary unit 120 moves from the duodenum 131 to the small intestine 132 toward the distal direction. In this case, the distal direction (the second axial direction) is a direction toward which the sectional area of the lumen 105 gradually decreases.

In the state that the rotary unit 120 moves from the duodenum 131 to the small intestine 132 toward the tip direction (the second axial direction) when the spiral fin portion 121 is in the neutral state, the projecting portion 129 of the cover member 128 first comes in contact with the luminal paries 106 only in a first action region U1 located in the distal-direction-side part of the rotary unit 120. Consequently, in the rotary unit 120, a first pressing force G1 toward the inner peripheral direction acts from the luminal paries 106 only onto the first action region U1. By the first pressing force G1, the fin diametric dimension between the longitudinal axis C and the spiral fin portion 121 decreases from the neutral state in the first action region U1. At this time, in a part to the proximal direction (first axial direction) side with respect to the first action region U1, the projecting portion 129 of the cover member 128 does not come in contact with the luminal paries 106, and the pressing force in the inner peripheral direction does not act from the luminal paries 106.

Figure 16:
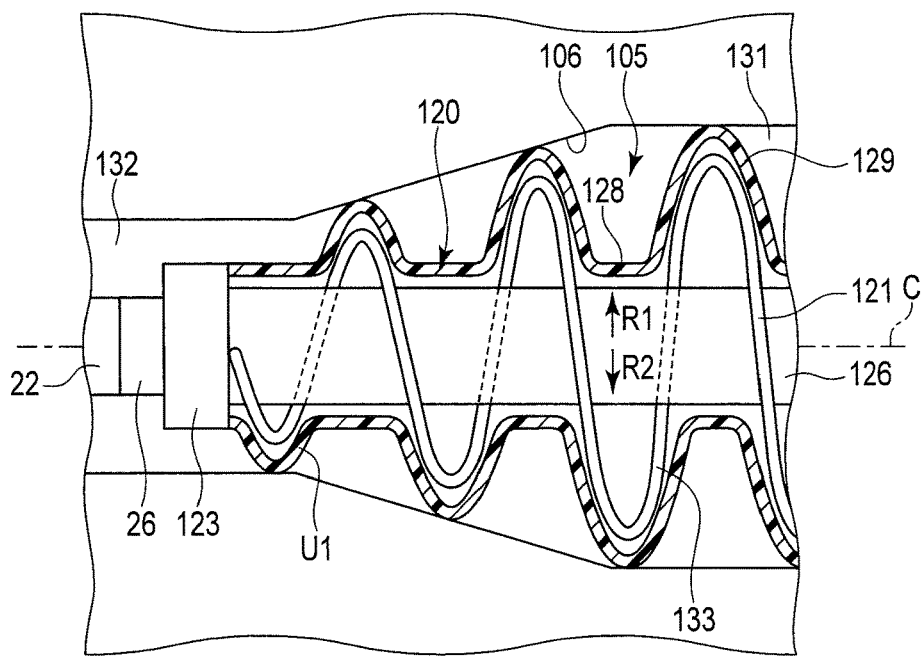
FIG. 16 is a schematic view showing a state in which the rotary unit is rotated from the state of FIG. 15 toward a first around-axis direction.

FIG. 16 is a view showing that the rotary unit 120 is rotated from the state of FIG. 15 toward the first around-axis direction (a direction of an arrow R1 of FIG. 16). In the rotary unit 120, the polygonal inner peripheral portion 127, which is the drive force receiving portion, is positioned to the proximal direction (first axial direction) side with respect to the spiral fin portion 121. That is, the first action region U1 of the rotary unit 120 is positioned away from the polygonal inner peripheral portion 127 in the directions parallel to the longitudinal axis C. Consequently, transmission properties of the rotary drive force from the polygonal inner peripheral portion 127 to the first action region U1 are not high. Therefore, as shown in FIG. 16, also when the rotary unit 120 is rotated from the state of FIG. 15 in the first around-axis direction, the rotation of the spiral fin portion 121 temporarily stops in the first action region U1 by the first pressing force G1 from the luminal paries 106.

On the other hand, in the neutral state of the spiral fin portion 121, the pressing force from the luminal paries 106 toward the inner peripheral direction does not act on the part to the proximal direction (first axial direction) side with respect to the first action region U1. Consequently, when the rotary unit 120 is rotated from the state of FIG. 15 toward the first around-axis direction, the spiral fin portion 121 rotates in the first around-axis direction in the part to the proximal direction side of the first action region U1. Therefore, as shown in FIG. 16, the spiral fin portion 121 moves toward the distal direction (the second axial direction) in the part to the proximal direction side with respect to the first action region U1, and the spiral fin portion 121 contracts from the neutral state along the longitudinal axis C in the part to the proximal direction side with respect to the first action region U1. Consequently, the amount of twisting of the spring member decreases, and the number of turns of the spiral fin portion 121 decreases from the neutral state in the part to the base direction side with respect to the first action region U1. The number of the turns of the spiral fin portion 121 decreases, and hence the fin diametric dimension between the longitudinal axis C and the spiral fin portion 121 increases from the neutral state in the part to the proximal direction side with respect to the first action region U1. Therefore, in the part to the base direction side with respect to the first action region U1, the fin diametric dimension is larger than the reference fin diametric dimension D0.

As described above, in the rotary unit 120, there is provided a fin dimension increase portion 133 by which when the rotary unit 120 rotates toward the first around-axis direction in the state that the first pressing force G1 in the inner peripheral direction acts only in the first action region U1, in the part to the proximal direction (first axial direction) side with respect to the first action region U1, the spiral fin portion 121 is contracted along the longitudinal axis C and the fin diametric dimension is increased from the neutral state. The fin diametric dimension increases in the part to the base direction side of the first action region U1, whereby the projecting portion 129 of the cover member 128 comes in contact with the luminal paries 106 in the part to the proximal direction side with respect to the first action region U1. Therefore, the projecting portion 129 comes in contact with the luminal paries 106 over the whole length in the directions parallel to the longitudinal axis C, and a contact area of the projecting portion 129 with the luminal paries 106 is large. The contact area of the projecting portion 129 with the luminal paries 106 is large, and hence the propelling force F1 which acts on the rotary unit 120 and the inserting section 2 increases. Consequently, when the rotary unit 120 moves through the portion where the sectional area gradually decreases (changes) from the duodenum 131 toward the small intestine 132, the inserting properties of the inserting section 2 are acquired. That is, when the rotary unit 120 moves through the portion between the duodenum 131 and the small intestine 132, moving properties of the inserting section 2 toward the distal direction (the second axial direction) parallel to the longitudinal axis C are acquired.

It is to be noted that as an example where the tip direction matches the direction toward which the sectional area of the lumen 105 decreases, the part between the duodenum 131 and the small intestine 132 has been described, but it is not limited to this example. For example, in an esophagus, there is a sectional area change portion where the sectional area of the lumen gradually decreases toward the stomach. When the inserting section 2 and the rotary unit 120 are inserted from the mouth to the stomach, the rotary unit 120 passes the sectional area change portion of the esophagus. Also in this case, the distal direction is a direction toward which the sectional area of the lumen decreases in the same manner as in the case where the rotary unit 120 passes the part between the duodenum 131 and the small intestine 132. Furthermore, the moving properties of the inserting section 2 toward the distal direction are acquired by the fin dimension increase portion 133 in the same manner as in the case where the rotary unit 120 passes the part between the duodenum 131 and the small intestine 132.

Figure 17:
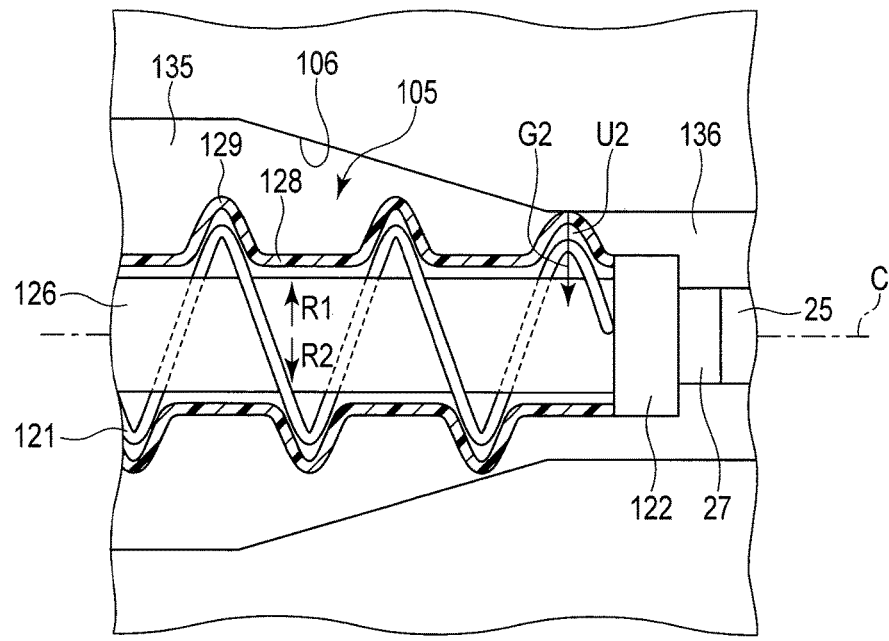
FIG. 17 is a schematic view showing a state in which the rotary unit according to the first reference example moves in the lumen from a cecum toward a sigmoid colon when the spiral fin portion is in the neutral state.

FIG. 17 is a view showing a state in which the rotary unit 120 moves in the lumen 105 from a cecum 135 toward a sigmoid colon 136 when the spiral fin portion 121 is in the neutral state. As shown in FIG. 17, when the inserting section 2 and the rotary unit 120 having been inserted from the anus up to the cecum 135 are removed, the rotary unit 120 moves from the cecum 135 to the sigmoid colon 136 toward the proximal direction. In this case, the proximal direction (the first axial direction) is a direction toward which a sectional area of the lumen 105 (the large intestine) decreases.

In the state in which the rotary unit 120 moves from the cecum 135 toward the sigmoid colon 136 in the base direction (the first axial direction) when the spiral fin portion 121 is in the neutral, the projecting portion 129 of the cover member 128 first comes in contact with the luminal paries 106 only in a second action region U2 located in the proximal-direction-side part of the rotary unit 120. Consequently, in the rotary unit 120, a second pressing force G2 in the inner peripheral direction acts from the luminal paries 106 only onto the second action region U2. By the second pressing force G2, the fin diametric dimension between the longitudinal axis C and the spiral fin portion 121 decreases from the neutral state in the second action region U2. At this time, in a part to the distal direction (second axial direction) side with respect to the second action region U2, the projecting portion 129 of the cover member 128 does not come in contact with the luminal paries 106, and the pressing force toward the inner peripheral direction does not act from the luminal paries 106.

Figure 18:
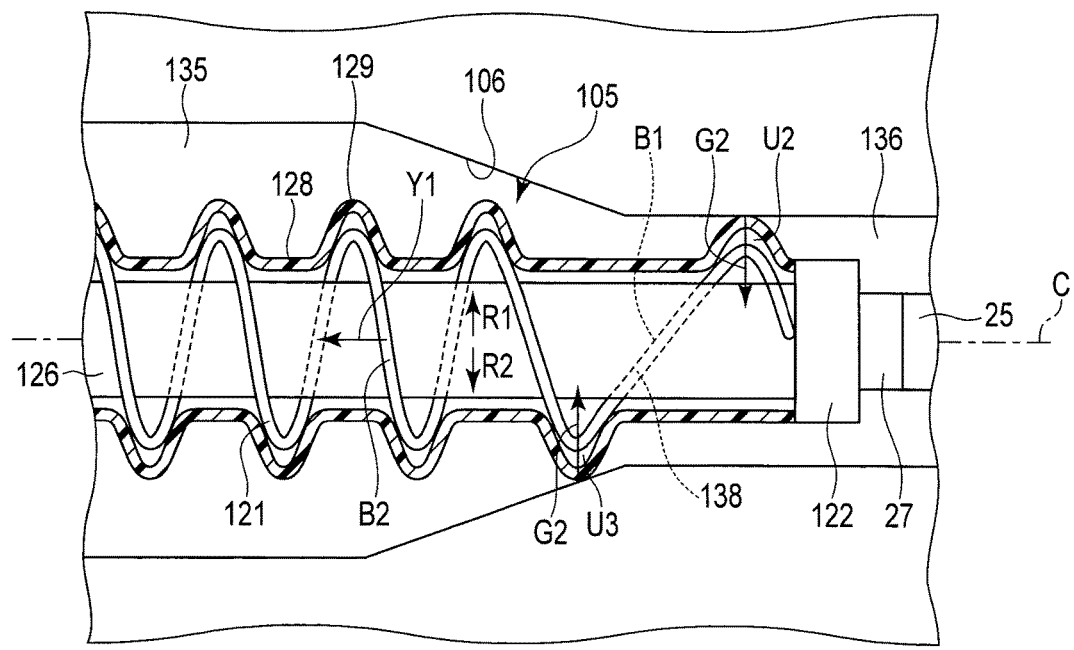
FIG. 18 is a schematic view showing a state in which the rotary unit is rotated from the state of FIG. 17 toward a second around-axis direction.

FIG. 18 is a view showing a state in which the rotary unit 120 is rotated from the state of FIG. 17 toward the second around-axis direction (a direction of an arrow R2 of FIG. 18). In the rotary unit 120, the polygonal inner peripheral portion 127 which is the drive force receiving portion is positioned to the proximal direction (first axial direction) side with respect to the spiral fin portion 121. That is, the second action region U2 of the rotary unit 120 is positioned in the vicinity of the polygonal inner peripheral portion 127 in the directions parallel to the longitudinal axis C. Consequently, the transmission properties of the rotary drive force from the polygonal inner peripheral portion 127 to the second operation region U2 are high. Therefore, as shown in FIG. 18, when the rotary unit 120 is rotated from the state of FIG. 17 in the second around-axis direction, the spiral fin portion 121 rotates toward the second around-axis direction against the second pressing force G2 from the luminal paries 106 in the second action region U2. Therefore, in the second action region U2, the spiral fin portion 121 moves toward the proximal direction (the first axial direction).

In the second action region U2, the spiral fin portion 121 moves toward the base direction against the second pressing force G2. Consequently, a third action region U3 located to the distal direction (second axial direction) side with respect to the second action region U2 comes in contact with the luminal paries 106, and the second pressing force G2 acts in the third action region U3. At this time, the second pressing force G2 acts only in a region between the second action region U2 and the third action region U3. The third action region U3 is located at an angular position away from the second action region U2 as much as about 180° in the directions around the longitudinal axis.

When the rotary unit 120 is rotated toward the second around-axis direction in the state that the second pressing force G2 acts only in the region between the second action region U2 and the third action region U3, an expansion region B1 is formed between the second action region U2 and the third action region U3. In the expansion region B1, the spiral fin portion 121 expands from the neutral state along the longitudinal axis C. The spiral fin portion 121 expands, and hence in the expansion region B1, the amount of twisting of the spring member increases, the fin diametric dimension between the longitudinal axis C and the spiral fin portion 121 decreases from the neutral state. Therefore, in the expansion region B1 between the second action region U2 and the third action region U3, the fin diametric dimension is smaller than the reference fin diametric dimension D0.

Furthermore, in the expansion region B1 between the second action region U2 and the third action region U3, the fin diametric dimension decreases from the neutral state, and the spiral fin portion 121 expands, whereby in a part to the distal direction (second axial direction) side with respect to the third action region U3, a pitch of the spiral fin portion 121 temporarily decreases from the neutral state. Consequently, in the part to the tip direction side with respect to the third action region U3, there is temporarily formed a contraction region B2 where the spiral fin portion 121 is contracted along the longitudinal axis C. In the contraction region B2, the fin diametric dimension between the longitudinal axis C and the spiral fin portion 121 does not increase from the neutral state. Consequently, in the contraction region B2, the projecting portion 129 of the cover member 128 does not come in contact with the luminal paries 106. Furthermore, in the contraction region B2, the spiral fin portion 121 contracts, and hence an elastic force Y1 acts toward the distal direction (the second axial direction).

Figure 19:
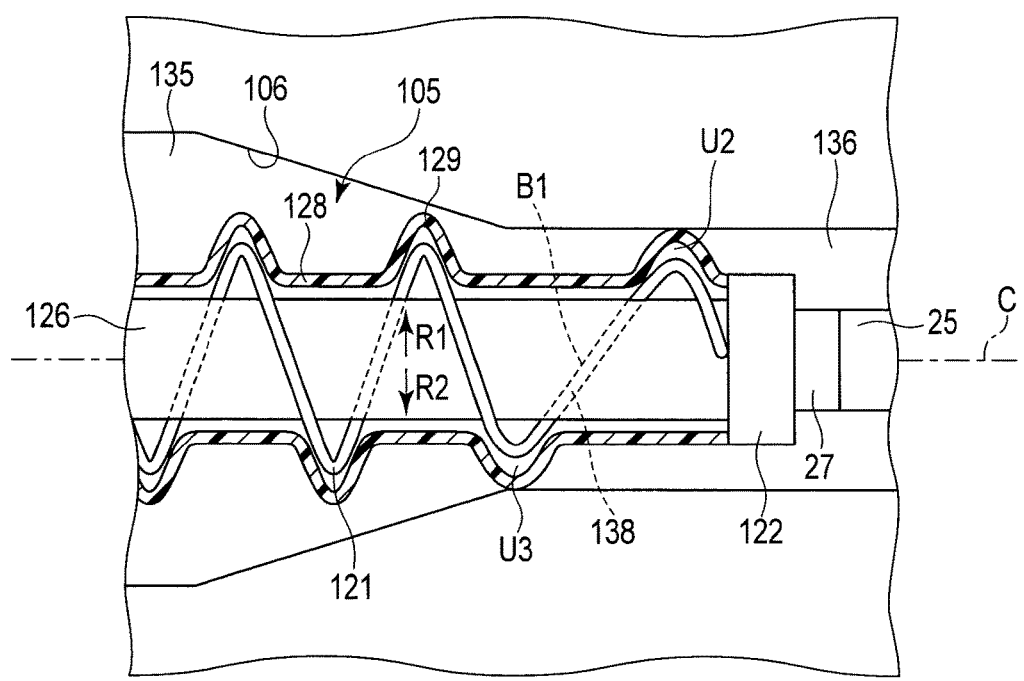
FIG. 19 is a schematic view showing a state in which the spiral fin portion is deformed from the state of FIG. 18 by an elastic force which acts in a contraction region.

FIG. 19 is a view showing a state in which the spiral fin portion 121 is deformed from the state of FIG. 18 by the elastic force Y1 which acts in the contraction region B2. As shown in FIG. 19, the elastic force Y1 is generated in the contraction region B2, whereby the spiral fin portion 121 moves toward the distal direction (the second axial direction) in the part to the distal direction side with respect to the third action region U3. Consequently, in the contraction region B2 where the spiral fin portion 121 is temporarily contracted, the spiral fin portion 121 returns to the neutral state by the elastic force Y1.

As described above, in the rotary unit 120, there is provided a fin dimension decrease portion 138 in which when the rotary unit 120 rotates toward the second around-axis direction in the state that the second pressing force G2 in the inner peripheral direction acts only in the region between the second action region U2 and the third action region U3, the spiral fin portion 121 is expanded along the longitudinal axis C and the fin diametric dimension is decreased from the neutral state between the second action region U2 and the third action region U3. The fin diametric dimension decreases between the second action region U2 and the third action region U3, whereby a dimension from the longitudinal axis C to an outer peripheral end of the rotary unit 120 decreases between the second action region U2 and the third action region U3. Consequently, when the rotary unit 120 moves through the part where the sectional area gradually decreases (changes) from the cecum 135 toward the sigmoid colon 136, the removing properties of the inserting section 2 are acquired. That is, when the rotary unit 120 moves through the portion between the cecum 135 and the sigmoid colon 136, the moving properties of the inserting section 2 toward the proximal direction (the first axial direction) parallel to the longitudinal axis C are acquired.

It is to be noted that as the example where the proximal direction matches the direction toward which the sectional area of the lumen 105 decreases, the part between the cecum 135 and the sigmoid colon 136 has been described, but it is not limited to this example.

Furthermore, in a state that the pressing force does not act on the rotary unit 120 in the inner peripheral direction, the spiral fin portion 121 is held in the neutral state by the cover member 128. Therefore, when the rotary unit 120 passes the part where the sectional area gradually changes and then the pressing force does not act from the luminal paries 106 onto the rotary unit 120 toward the inner peripheral direction, the spiral fin portion 121 is in the neutral state. Furthermore, when the pressing force toward the inner peripheral direction acts from the luminal paries 106 onto the rotary unit 120 over the whole length in the directions parallel to the longitudinal axis C, the fin diametric dimension from the proximal end to the distal end of the spiral fin portion 121 is substantially constant, and the fin diametric dimension is smaller than the reference fin diametric dimension in the neutral state.

As described above, in the rotary unit 120, the expansion and contraction state of the spiral fin portion 121 along the longitudinal axis C and the fin diametric dimension change in accordance with a change of the sectional area of the passed portion in the lumen 105 by the pressing force which acts from the luminal paries 106 and the rotary drive force transmitted to the polygonal inner peripheral portion 127 which is the drive force receiving portion. Therefore, the expansion and contraction state of the spiral fin portion 121 along the longitudinal axis C and the fin diametric dimension change so that the spiral fin portion easily moves in the directions parallel to the longitudinal axis C, in accordance with the change of the sectional area of the passed part in the lumen 105.

Figure 20:
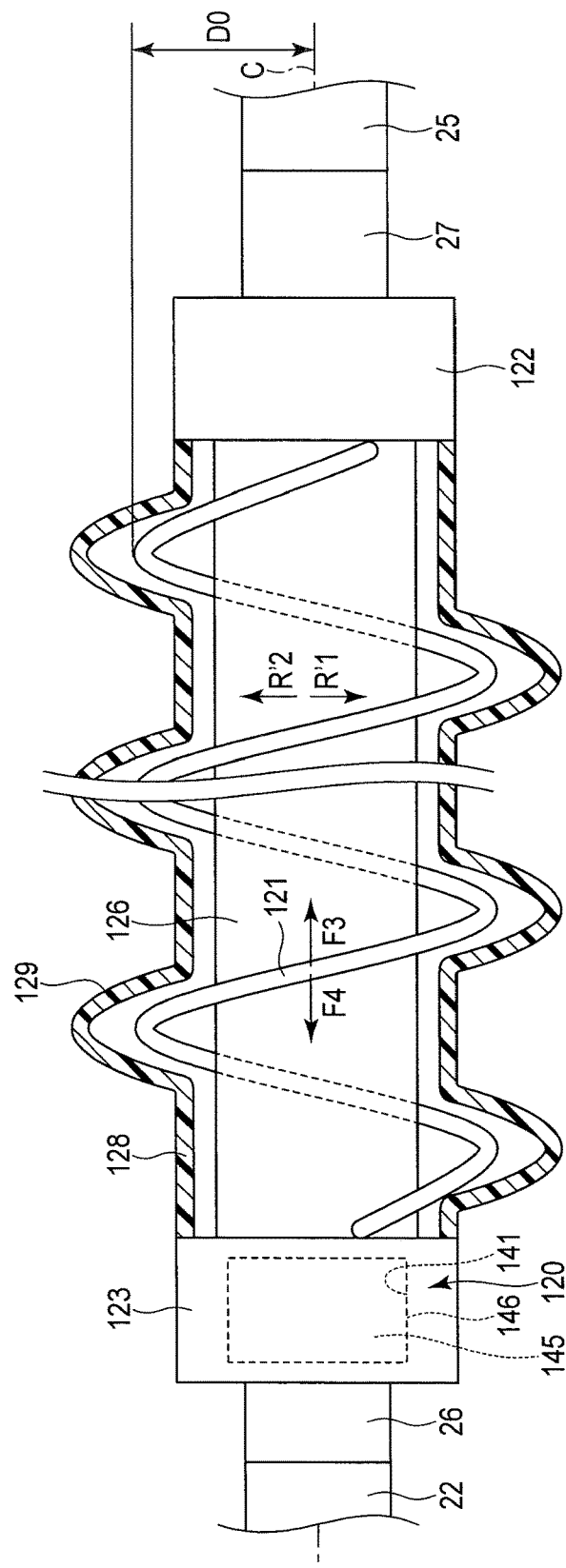
FIG. 20 is a side view schematically showing a rotary unit according to a second reference example, and only shows a cover member in a cross section.

It is to be noted that in the first reference example, the polygonal inner peripheral portion 127 which is the drive force receiving portion is provided to the proximal direction side with respect to the spiral fin portion 121, but it is not limited to this example. For example, as a second reference example shown in FIG. 20, a polygonal inner peripheral portion 141 which is a drive force receiving portion may be provided to a distal direction side with respect to a spiral fin portion 121, in place of the polygonal inner peripheral portion 127. The polygonal inner peripheral portion 141 is positioned on an inner peripheral portion of a distal-side connecting member 123. In the present reference example, a distal direction is a first axial direction, and a proximal direction is a second axial direction. In this case, a clockwise direction (a direction of an arrow R'1 of FIG. 20) seen from a tip direction side (a first axial direction side) is a first around-axis direction, and a counterclockwise direction (a direction of an arrow R'2 of FIG. 20) seen from the distal direction side (the first axial side) is a second around-axis direction. Furthermore, the distal-side connecting member 123 is a first connecting member, and the proximal-side connecting member 122 is a second connecting member.

Furthermore, in the present reference example, a rotary tubular member 145 is provided in place of the rotary tubular member 65. The rotary tubular member 145 is rotatable integrally with a rotary unit 120 with respect to an inserting section 2 in directions around a longitudinal axis. The rotary tubular member 145 is attached to a first relay connecting section 26 positioned between a bending section 22 and a first flexible tube section 23. The rotary tubular member 145 is provided with a polygonal outer peripheral portion 146 in the same manner as in the rotary tubular member 65. The polygonal inner peripheral portion 141 of the tip-side connecting member 123 comes in close contact with the polygonal outer peripheral portion 146 of the rotary tubular member 145, whereby the rotary unit 120 is attached to the rotary tubular member 145.

When the directions are defined as described above, the spiral fin portion 121 is positioned toward the first around-axis direction as the spiral fin portion extends from the distal direction (the first axial direction) toward the proximal direction (the second axial direction). When the rotary unit 120 is rotated toward the first around-axis direction in a state that a projecting portion 129 of a cover member 128 of the rotary unit 120 is in contact with a luminal paries 106, a propelling force F3 toward the proximal direction (the second axial direction) acts on the rotary unit 120 and the inserting section 2. On the other hand, when the rotary unit 120 is rotated toward the second around-axis direction in the state that the projecting portion 129 of the cover member 128 of the rotary unit 120 is in contact with the luminal paries 106, a propelling force F4 toward the distal direction (the first axial direction) acts on the rotary unit 120 and the inserting section 2. A principle responsible for the generation of the propelling forces F3 and F4 is similar to a principle responsible for the generation of the propelling forces F1 and F2 in the first embodiment and the first reference example.

Figure 21:
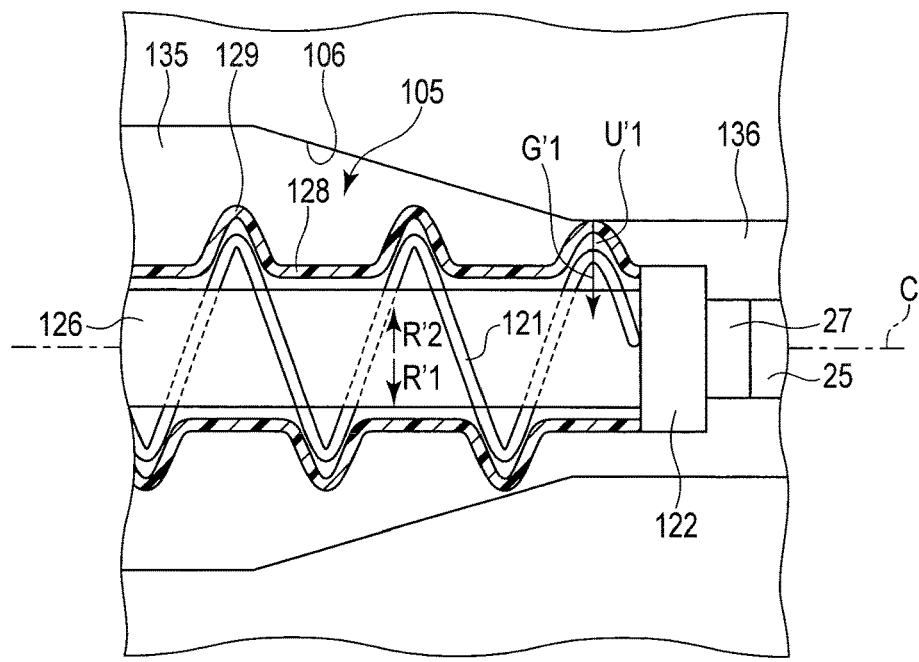
FIG. 21 is a schematic view showing a state in which the rotary unit according to the second reference example moves in a lumen from a cecum toward a sigmoid colon when a spiral fin portion is in a neutral state.

FIG. 21 is a view showing a state in which the rotary unit 120 moves in a lumen 105 from a cecum 135 toward a sigmoid colon 136 when the spiral fin portion 121 is in a neutral state. As shown in FIG. 21, when the inserting section 2 and the rotary unit 120 having been inserted from an anus up to the cecum 135 are removed, the rotary unit 120 moves from the cecum 135 toward the sigmoid colon 136 in the proximal direction. In this case, the proximal direction (the second axial direction) is a direction toward which a sectional area of the lumen 105 decreases.

In the state that the rotary unit 120 moves from the cecum 135 to the sigmoid colon 136 toward the base direction (the second axial direction) when the spiral fin portion 121 is in the neutral state, the projecting portion 129 of the cover member 128 first comes in contact with the luminal paries 106 only in a first action region U'1 located to a proximal-direction-side part of the rotary unit 120. Consequently, in the rotary unit 120, a first pressing force G'1 in an inner peripheral direction acts from the luminal paries 106 only in the first action region U'1. By the first pressing force G'1, a fin diametric dimension between a longitudinal axis C and the spiral fin portion 121 decreases from the neutral state in the first action region U'1. At this time, in a part to the distal direction (first axial direction) side with respect to the first action region U'1, the projecting portion 129 of the cover member 128 does not come in contact with the luminal paries 106, and the pressing force toward the inner peripheral direction does not act from the luminal paries 106.

Figure 22:
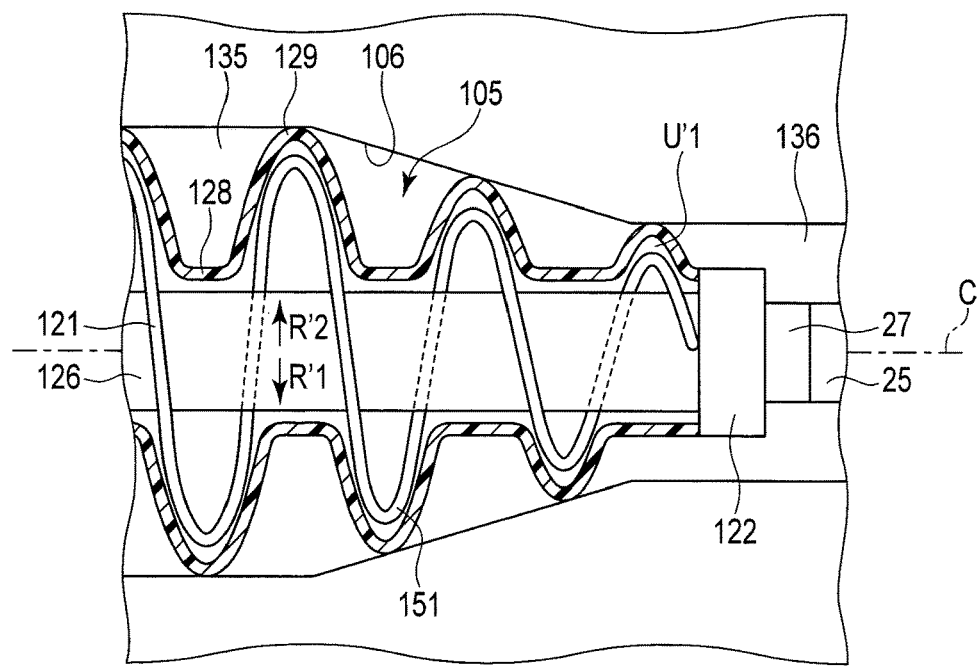
FIG. 22 is a schematic view showing a state in which the rotary unit is rotated from the state of FIG. 21 in a first around-axis direction.

FIG. 22 is a view showing a state in which the rotary unit 120 is rotated from the state of FIG. 21 toward the first around-axis direction (a direction of an arrow R'1 of FIG. 22). In the rotary unit 120, the polygonal inner peripheral portion 141 which is the drive force receiving portion is positioned to the distal direction (first axial direction) side with respect to the spiral fin portion 121. That is, the first action region U'1 of the rotary unit 120 is positioned away from the polygonal inner peripheral portion 141 in directions parallel to the longitudinal axis C. Consequently, transmission properties of the rotary drive force from the polygonal inner peripheral portion 141 to the first action region U'1 are not high. Therefore, as shown in FIG. 22, also when the rotary unit 120 is rotated from the state of FIG. 21 in the first around-axis direction, the rotation of the spiral fin portion 121 temporarily stops in the first action region U'1 by the first pressing force G'1 from the luminal paries 106.

On the other hand, the pressing force from the luminal paries 106 toward the inner peripheral direction does not act in the part to the distal direction (first axial direction) side of the first action region U'1 when the spiral fin portion 121 is in the neutral state. Consequently, when the rotary unit 120 is rotated from the state of FIG. 21 toward the first around-axis direction, the spiral fin portion 121 rotates in the first around-axis direction in the part to the tip direction side with respect to the first action region U'1. Therefore, as shown in FIG. 22, the spiral fin portion 121 moves toward the proximal direction (the second axial direction) in the part to the distal direction side with respect to the first action region U'1, and the spiral fin portion 121 contracts from the neutral state along the longitudinal axis C in the part to the tip direction side with respect to the first action region U'1. Consequently, in the part to the distal direction-side with respect to the first action region U'1, the number of turns of the spiral fin portion 121 decreases from the neutral state. The number of the turns of the spiral fin portion 121 decreases, and hence the fin diametric dimension between the longitudinal axis C and the spiral fin portion 121 increases from the neutral state in the part to the distal direction side of the first action region U'1. Therefore, in the part to the distal direction side with respect to the first action region U'1, the fin diametric dimension is larger than a reference fin diametric dimension D0.

As described above, in the rotary unit 120, there is provided a fin dimension increase portion 151 in which when the rotary unit 120 rotates toward the first around-axis direction in the state that the first pressing force G'1 in the inner peripheral direction acts only in the first action region U'1, the spiral fin portion 121 is contracted along the longitudinal axis C and the fin diametric dimension is increased from the neutral state in the part to the distal direction (first axial direction) side with respect to the first action region U'1. The fin diametric dimension increases in the part to the tip direction side of the first action region U'1, whereby the projecting portion 129 of the cover member 128 comes in contact with the luminal paries 106 in the part to the distal direction side with respect to the first action region U'1. Therefore, the projecting portion 129 comes in contact with the luminal paries 106 over the whole length in the directions parallel to the longitudinal axis C, and a contact area of the projecting portion 129 with the luminal paries 106 is large. The contact area of the projecting portion 129 with the luminal paries 106 is large, whereby the propelling force F3, which acts on the rotary unit 120 and the inserting section 2, increases. Consequently, when the rotary unit 120 moves through a part where a sectional area gradually decreases (changes) from the cecum 135 toward the sigmoid colon 136, removing properties of the inserting section 2 are acquired. That is, when the rotary unit 120 moves toward the base direction (the second axial direction) toward which the sectional area decreases in the part where the sectional area of the lumen 105 gradually changes, moving properties of the inserting section 2 in the proximal direction (the second axial direction) parallel to the longitudinal axis C are acquired.

Figure 23:
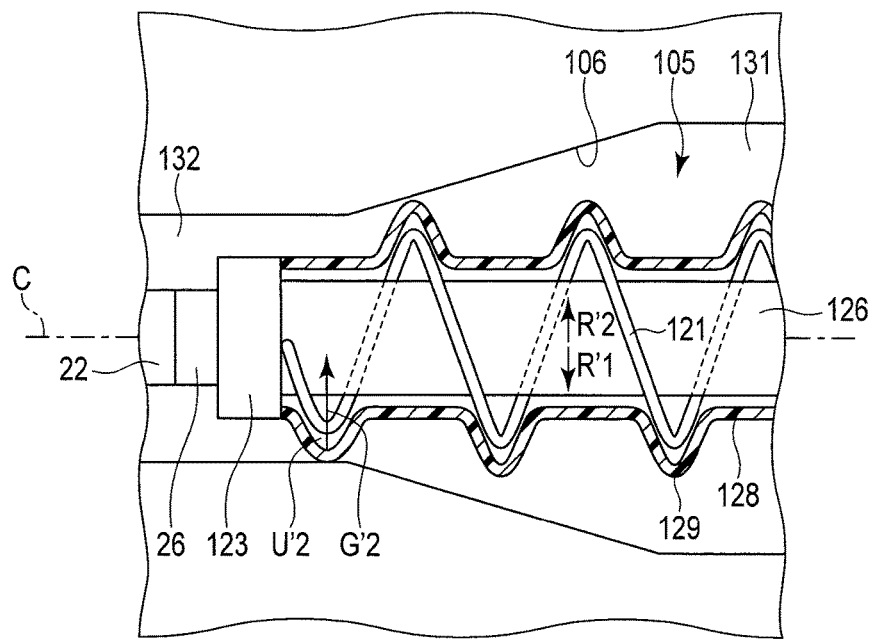
FIG. 23 is a schematic view showing a state in which the rotary unit according to the second reference example moves in the lumen from a duodenum toward a small intestine when the spiral fin portion is in the neutral state.

FIG. 23 is a view showing a state in which the rotary unit 120 moves in the lumen 105 from a duodenum 131 toward a small intestine 132 when the spiral fin portion 121 is in the neutral state. As shown in FIG. 23, when the inserting section 2 and the rotary unit 120 are inserted from a mouth up to the small intestine 132, the rotary unit 120 moves from the duodenum 131 to the small intestine 132 toward the distal direction. In this case, the distal direction (the first axial direction) is the direction toward which the sectional area of the lumen 105 decreases.

In the state that the rotary unit 120 moves from the duodenum 131 to the small intestine 132 toward the tip direction (the first axial direction) when the spiral fin portion 121 is in the neutral state, the projecting portion 129 of the cover member 128 first comes in contact with the luminal paries 106 only in a second action region U'2 located in the distal-direction-side part of the rotary unit 120. Consequently, in the rotary unit 120, a second pressing force G'2 in the inner peripheral direction acts from the luminal paries 106 only in the second action region U'2. By the second pressing force G'2, the fin diametric dimension between the longitudinal axis C and the spiral fin portion 121 decreases from the neutral state in the second action region U'2. At this time, in a part to the proximal direction (second axial direction) side of the second action region U'2, the projecting portion 129 of the cover member 128 does not come in contact with the luminal paries 106, and the pressing force toward the inner peripheral direction does not act from the luminal paries 106.

Figure 24:
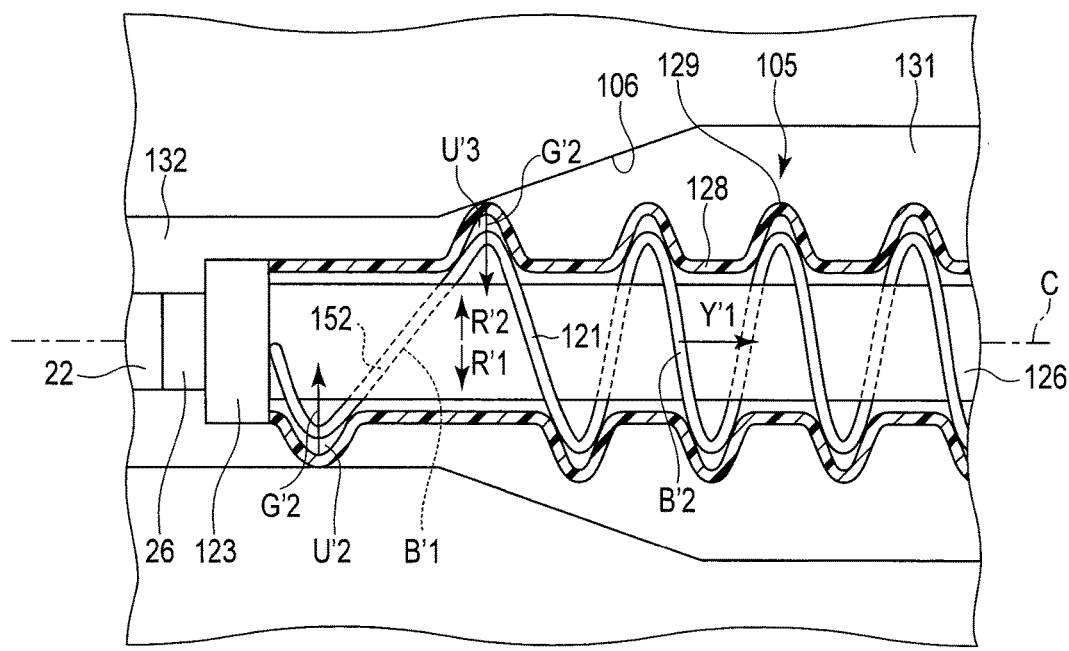
FIG. 24 is a schematic view showing a state in which the rotary unit is rotated from the state of FIG. 23 in a second around-axis direction.

FIG. 24 is a view showing a state in which the rotary unit 120 is rotated from the state of FIG. 23 toward the second around-axis direction (a direction of an arrow R'2 of FIG. 24). In the rotary unit 120, the polygonal inner peripheral portion 141 which is the drive force receiving portion is positioned to the distal direction (first axial direction) side with respect to the spiral fin portion 121. That is, the second action region U'2 of the rotary unit 120 is positioned in the vicinity of the polygonal inner peripheral portion 141 in the directions parallel to the longitudinal axis C. Consequently, the transmission properties of the rotary drive force from the polygonal inner peripheral portion 141 to the second action region U'2 are high. Therefore, as shown in FIG. 24, when the rotary unit 120 is rotated from the state of FIG. 23 in the second around-axis direction, the spiral fin portion 121 rotates toward the second around-axis direction against the second pressing force G'2 from the luminal paries 106 in the second action region U'2. Therefore, in the second action region U'2, the spiral fin portion 121 moves toward the distal direction (the first axial direction).

In the second action region U'2, the spiral fin portion 121 moves toward the tip direction against the second pressing force G'2. Consequently, a third action region U'3 located to the proximal direction (second axial direction) side with respect to the second action region U'2 comes in contact with the luminal paries 106, and the second pressing force G'2 acts in the third action region U'3. In this case, the second pressing force G'2 acts only in a region between the second action region U'2 and the third action region U'3. The third action region U'3 is located at an angular position away from the second action region U'2 by as much as about 180° in the directions around the longitudinal axis.

When the rotary unit 120 is rotated toward the second around-axis direction in the state that the second pressing force G'2 acts only in a region between the second action region U'2 and the third action region U'3, an expansion region B'1 is formed between the second action region U'2 and the third action region U'3. In the expansion region B'1, the spiral fin portion 121 expands along the longitudinal, axis C from the neutral state. The spiral fin portion 121 expands, whereby in the expansion region B'1, the fin diametric dimension between the longitudinal axis C and the spiral fin portion 121 decreases from the neutral state. Therefore, in the expansion region B'1 between the second action region U'2 and the third action region U'3, the fin diametric dimension is smaller than the reference fin diametric dimension D0.

Furthermore, in the expansion region B'1 between the second action region U'2 and the third action region U'3, the fin diametric dimension decreases from the neutral state, and the spiral fin portion 121 expands, whereby in a part to the proximal direction (second axial direction) side with respect to the third action region U'3, a pitch of the spiral fin portion 121 temporarily decreases from the neutral state. Consequently, in the part to the base direction side with respect to the third action region U'3, there is temporarily formed a contraction region B'2 where the spiral fin portion 121 contracts along the longitudinal axis C. In the contraction region B'2, the fin diametric dimension between the longitudinal axis C and the spiral fin portion 121 does not increase from the neutral state. Consequently, in the contraction region B'2, the projecting portion 129 of the cover member 128 does not come in contact with the luminal paries 106. Furthermore, in the contraction region B'2, the spiral fin portion 121 contracts, and hence an elastic force Y'1 acts toward the proximal direction (the second axial direction).

FIG. 25 is a view showing a state in which the spiral fin portion 121 is deformed from the state of FIG. 24 by the elastic force Y'1 which acts in the contraction region B'2. As shown in FIG. 25, the elastic force Y'1 is generated in the contraction region B'2, whereby the spiral fin portion 121 moves toward the proximal direction (the second axial direction) in the part to the proximal direction side with respect to the third action region U'3. Consequently, in the contraction region B'2 where the spiral fin portion 121 is temporarily contracted, the spiral fin portion 121 returns to the neutral state by the elastic force Y'1.

As described above, in the rotary unit 120, there is provided a fin dimension decrease portion 152 in which when the rotary unit 120 rotates toward the second around-axis direction in the state that the second pressing force G'2 in the inner peripheral direction acts only in the region between the second action region U'2 and the third action region U'3, the spiral fin portion 121 is expanded along the longitudinal axis C and the fin diametric dimension is decreased from the neutral state between the second action region U'2 and the third action region U'3. The fin diametric dimension decreases in the region between the second action region U'2 and the third action region U'3, whereby a dimension from the longitudinal axis C to an outer peripheral end of the rotary unit 120 decreases in the region between the second action region U'2 and the third action region U'3. Consequently, when the rotary unit 120 moves through the part where the sectional area gradually decreases (changes) from the duodenum 131 toward the small intestine 132, inserting properties of the inserting section 2 are acquired. That is, when the rotary unit 120 moves toward the distal direction (the first axial direction) toward which the sectional area decreases in the part where the sectional area of the lumen 105 gradually changes, the moving properties of the inserting section 2 in the tip direction (the first axial direction) parallel to the longitudinal axis C are acquired.

In the above-mentioned reference example, the spiral fin portion 121 of the rotary unit 120 may be positioned toward the first around-axis direction which is one of the directions around the longitudinal axis as the spiral fin portion extends from the first axial direction (one of the proximal direction and the distal direction) toward the second axial direction (the other of the proximal direction and the distal direction). Furthermore, the drive force receiving portion (e.g., the polygonal inner peripheral portion 127 or the polygonal inner peripheral portion 141) which receives the rotary drive force from the drive unit 80 may be disposed to the first axial direction side with respect to the spiral fin portion 121 in the rotary unit 120. Furthermore, the rotary unit rotates toward the first around-axis direction in the state that the first pressing force (G1; G'1) toward the inner peripheral direction side acts only in the first action region (U1; U'1) provided in the second-axial-direction-side part in the rotary unit 120, whereby the spiral fin portion 121 may contract along the longitudinal axis C and the fin diametric dimension may increase from the neutral state in a part to the first axial direction side with respect to the first action region (U1; U'1) by the fin dimension increase portion (133; 151). Furthermore, the rotary unit 120 rotates toward the second around-axis direction which is the direction opposite to the first around-axis direction in the state that the second pressing force (G2; G'2) toward the inner peripheral direction acts only in the region between the second action region (U2; U'2) located in the first-axial-direction-side part and the third action region (U3; U'3) located to the second axial direction side with respect to the second action region (U2; U'2) in the rotary unit 120, whereby the spiral fin portion 121 may expand along the longitudinal axis C and the fin diametric dimension may decrease from the neutral state in the region between the second action region (U2; U'2) and the third action region (U3; U'3).

(Other Modifications)

Furthermore, as a fourth modification shown in FIG. 26, a rotary unit (tubular unit) 160 may be attached to an inserting section 2. The rotary unit 160 includes a tubular unit main body 161. Furthermore, the rotary unit 160 includes at least one tapered portion at the end of the rotary unit 160. For example, a proximal-side taper tubular portion 92, which is a first taper tubular portion having a constitution similar to the first embodiment, is contiguous to a proximal direction side (a first axial side) of the unit main body 161. An outer diameter of the proximal-side taper tubular portion 92 becomes smaller toward the proximal direction side whereby a part of a projection member is projected on the tapered portion. On an outer peripheral portion 102 of the base-side taper tubular portion 92, a proximal-side projecting portion 96 which is a first projecting portion projected toward an outer peripheral direction is extended in the same manner as in the first embodiment. The proximal-side projecting portion 96 is wound toward a first around-axis rotation direction (a direction of an arrow R1 of FIG. 26) as the base-side projecting portion extends from the proximal direction (a first axial direction) toward a distal direction (a second axial direction).

A distal-side taper tubular portion 93, which is a second taper tubular portion having a constitution similar to the first embodiment, is contiguous to a distal direction side (a second axial side) of the tubular unit main body portion 161. An outer diameter of the distal-side taper tubular portion 93 becomes smaller toward the distal direction side. On an outer peripheral portion 103 of the tip-side taper tubular portion 93, a distal-side projecting portion 97 which is a second projecting portion projected toward the outer peripheral direction is extended in the same manner as in the first embodiment. The distal-side projecting portion 97 is wound toward the first around-axis direction as the tip-side projecting portion extends from the proximal direction (the first axial direction) toward the distal direction (the second axial direction).

Furthermore, the unit main body 161 includes a corrugate tube 125 and a jacket 126 having constitutions similar to the first reference example and the second reference example. Furthermore, on an outer peripheral portion of the jacket 126, a spiral fin portion 121 is spirally extended about a longitudinal axis C in the same manner as in the first reference example and the second reference example. The spiral fin portion 121 is positioned toward the first around-axis direction as the spiral fin portion extends from the proximal direction (the first axial direction) toward the distal direction (the second axial direction). A proximal end of the spiral fin portion 121 is connected to the proximal-side taper tubular portion 92, and a distal end of the spiral fin portion 121 is connected to the distal-side taper tubular portion 93. Therefore, the spiral fin portion 121 is not contiguous to the proximal-side projecting portion 96. Furthermore, the spiral fin portion 121 is not contiguous to the distal-side projecting portion 97. Furthermore, an outer peripheral direction side of the spiral fin portion 121 is covered with a cover member 128. In the present modification, a proximal portion of the unit main body 161 is provided with a polygonal inner peripheral portion 162. The polygonal inner peripheral portion 162 of the rotary unit 160 comes in close contact with a polygonal outer peripheral portion 66 of a rotary tubular member 65, and the rotary unit 160 is attached to an outer peripheral direction of the rotary tubular member 65.

In the rotary unit (30; 160) of the above-mentioned embodiment and modifications, the first taper tubular portion (corresponding to the proximal-side taper tubular portion 92 or the distal-side taper tubular portion 93) may be contiguous to the first axial direction side (corresponding to the proximal direction side or the distal direction side) of the unit main body portion (91; 161). Furthermore, the first unit end (corresponding to the unit proximal end E1 or the unit distal end E2) which is the first-axial-direction-side end of the rotary unit (30; 160) may be positioned in the first taper tubular portion (corresponding to 92 or 93). The outer diameter of the first taper tubular portion (corresponding to 92 or 93) becomes smaller toward the first axial direction. Furthermore, on the outer peripheral portion (corresponding to 102 or 103) of the first taper tubular portion (corresponding to 92 or 93) of the rotary unit (30; 160), the first projecting portion (corresponding to the proximal-side projecting portion 96 or the distal-side projecting portion 97) projected toward the outer peripheral direction may be extended. Furthermore, the first projecting portion may be wound toward the first around-axis direction (the direction shown by the arrow R1 of FIG. 1 or the direction shown by the arrow R2 of FIG. 1) which is one of the directions around the longitudinal axis as the first projecting portion extends from the first axial direction (one of the distal direction and the proximal direction) toward the second axial direction (the other of the distal direction and the proximal direction).

Hereinafter, characteristic particulars of the above-mentioned reference examples will be described as additional notes.

Notes (Additional Note 1)
An insertion device comprising:
an inserting section extended along a longitudinal axis from a first axial direction toward a second axial direction which is a direction opposite to the first axial direction;
a rotary unit which is provided to an outer peripheral direction side of the inserting section, and which is rotatable with respect to the inserting section in directions around the longitudinal axis;
a spiral fin portion which is positioned toward a first around-axis direction that is one of the directions around the longitudinal axis as the spiral fin portion extends from the first axial direction toward the second axial direction in the rotary unit, and which is expandably and contractibly extended along the longitudinal axis, the fin portion being in a neutral state when a pressing force does not act onto the rotary unit toward an inner peripheral direction;
a base section which is provided in the inserting section, and to which the rotary unit is attached in a rotatable state with respect to the inserting section in the directions around the longitudinal axis;
a drive force receiving portion which is provided to the first axial direction side with respect to spiral fin portion in the rotary unit, and which is configured to receive a rotary drive force to rotate the rotary unit in one of the directions around the longitudinal axis;
a drive unit which is attached to the base section, and which is driven so as to transmit the rotary drive force to the drive force receiving portion;
a fin dimension increase portion in which when the rotary unit rotates toward the first around-axis direction by the rotary drive force in a state that a first pressing force toward the inner peripheral direction acts only in a first action region located in a second-axial-direction-side part of the rotary unit, the spiral fin portion is configured to be contracted along the longitudinal axis in a part to the first axial direction side with respect to the first action region and a fin diametric dimension between the longitudinal axis and the spiral fin portion is configured to be increased from the neutral state in the part to the first axial direction side with respect to the first action region; and
a fin dimension decrease portion in which when the rotary unit rotates toward a second around-axis direction which is a direction opposite to the first around-axis direction by the rotary drive force in a state that a second pressing force toward the inner peripheral direction acts only in a region between a second action region located in the first-axial-direction-side part and a third action region located to the second axial direction side with respect to the second action region in the rotary unit, the spiral fin portion is configured to be expanded along the longitudinal axis between the second action region and the third action region, and the fin diametric dimension between the longitudinal axis and the spiral fin portion is configured to be decreased from the neutral state between the second action region and the third action region.

(Additional Note 2)
The insertion device according to the additional note 1, wherein by the fin dimension increase portion, the rotation of the spiral fin portion is configured to be temporarily stopped by the first pressing force in the first action region, and the spiral fin portion is configured to be rotated toward the first around-axis rotation direction in the part to the first axial direction side with respect to the first action region, thereby contracting the spiral fin portion.

(Additional Note 3)
The insertion device according to the additional note 1, wherein by the fin dimension increase portion, the number of turns of the spiral fin portion is configured to be decreased in the part to the first axial direction side with respect to the first action region by the contraction of the spiral fin portion, thereby increasing the fin diametric dimension from the neutral state.

(Additional Note 4)
The insertion device according to the additional note 1, wherein the fin dimension decrease portion is configured to form an expansion region where the spiral fin portion expands along the longitudinal axis between the second action region and the third action region, when the second pressing force acts only in the region between the second action region and the third action region disposed at an angular position away from the second action region by as much as about 180° in the directions around the longitudinal axis.

(Additional Note 5)
The insertion device according to the additional note 4, wherein the fin dimension decrease portion is configured to temporarily form, in a part to the second axial direction side with respect to the third action region, a contraction region where the spiral fin portion is contracted along the longitudinal axis without increasing the fin diametric dimension from the neutral state.

(Additional Note 6)
The insertion device according to the additional note 1, wherein by the fin dimension decrease portion, the spiral fin portion is configured to be rotated toward the second around-axis direction against the second pressing force in the second action region.

(Additional Note 7)

The insertion device according to the additional note 1, wherein the rotary unit includes:

a first connecting member which is provided with the drive force receiving portion, and to which a first-axial-direction-side end of the spiral fin portion is connected;

a second connecting member to which a second-axial-direction-side end of the spiral fin portion is connected; and a tube member which is extended along the longitudinal axis between the first connecting member and the second connecting member, and which is positioned to the inner peripheral direction side of the spiral fin portion, the tube member being expandable and contractible along the longitudinal axis in accordance with the expansion and contraction of the spiral fin portion.

(Additional Note 8)

The insertion device according to the additional note 1, wherein the rotary unit includes a cover member which covers an outer peripheral side of the spiral fin portion, and which is elastically deformed in accordance with the expansion and contraction of the spiral fin portion and a change of the fin diametric dimension, the cover member being configured to hold the spiral fin portion in the neutral state in a state that the pressing force does not act on the rotary unit toward the inner peripheral direction.

(Additional Note 9)

The insertion device according to the additional note 1, wherein the drive unit is configured to rotate the rotary unit toward the first around-axis direction, thereby allowing a propelling force toward the second axial direction to act on the inserting section and the rotary unit, and the drive unit is configured to rotate the rotary unit toward the second around-axis direction, thereby allowing a propelling force toward the first axial direction to act on the inserting section and the rotary unit.

(Additional Note 10)

The insertion device according to the additional note 1, wherein the spiral fin portion is positioned toward the first around-axis direction, as the spiral fin portion extends from a proximal direction which is the first axial direction toward a distal direction which is the second axial direction.

(Additional Note 11)

The insertion device according to the additional note 1, wherein the spiral fin portion is positioned toward the first around-axis direction, as the spiral fin portion extends from a distal direction which is the first axial direction toward a proximal direction which is the second axial direction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A rotary unit through which an inserting section extended from a first axial direction toward a second axial direction along a longitudinal axis is inserted when one of directions along the longitudinal axis is the first axial direction and a direction opposite to the first axial direction is the second axial direction, the rotary unit being attached to a base section of the inserting section, the rotary unit being rotatable with respect to the inserting section in directions around the longitudinal axis, the rotary unit comprising:

a tubular unit main body portion extended along the longitudinal axis, an outer diameter of the unit main body portion being constant from a first-axial-direction-side end of the unit main body portion to a second-axial-direction-side end of the unit main body portion;

a first taper tubular portion which is provided on a first axial direction side with respect to the unit main body portion, a first-axial-direction-side end of the first taper tubular portion forming a first-axial-direction-side end of the rotary unit, a second-axial-direction-side end of the first taper tubular portion being contiguous with the first-axial-direction-side end of the unit main body portion, an outer diameter of the first taper tubular portion becoming smaller toward the first axial direction;

a first projecting portion which is extended on an outer peripheral portion of the first taper tubular portion between the first-axial-direction-side end of the rotary unit and the second-axial-direction-side end of the first taper tubular portion in a state projecting toward an outer peripheral direction, the first projecting portion being spirally extended around the longitudinal axis, a first projection diametric dimension between the longitudinal axis and a projection projecting end of the first projecting portion becoming larger from the first axial direction toward the second axial direction in the first projecting portion; and a fin portion which is extended on an outer peripheral portion of the unit main body portion in a state projecting toward the outer peripheral direction, the fin portion being spirally extended around the longitudinal axis, a first-axial-direction-side end of the fin portion being located at the first-axial-direction-side end of the unit main body portion or on a second axial direction side with respect to the first-axial-direction-side end of the unit main body portion, a fin diametric dimension between the longitudinal axis and a fin projecting end of the fin portion becoming larger from the first-axial-direction-side end of the fin portion toward a first reference position, the first reference position being located on the second axial direction side with respect to the first-axial-direction-side end of the fin portion, a projecting amount of the fin portion from the outer peripheral portion of the unit main body portion becoming larger toward the first reference position in a region between the first-axial-direction-side end of the unit main body portion and the first reference position, wherein the first taper tubular portion is a proximal-side taper tubular portion positioned on a proximal direction side that is the first axial direction side with respect to the unit main body portion, wherein the outer peripheral portion of the first taper tubular portion on which the first projecting portion is provided is contiguous to an outer peripheral portion of the inserting section at the first-axial-direction-side end of the rotary unit, and wherein the first-axial-direction-side end of the rotary unit is movable with respect to the outer peripheral portion of the inserting section when the rotary unit rotates with respect to the inserting section in one of the directions around the longitudinal axis.

2. The rotary unit according to claim 1, wherein the first projecting portion is one of a plurality of first projecting portions which are provided between the first-axial-direction-side end of the first taper tubular portion and the second-axial-direction-side end of the first taper tubular portion, the first projecting portions being disposed away from one another in the directions around the longitudinal axis.

3. The rotary unit according claim 1,
wherein a second-axial-direction-side end of the first projecting portion is contiguous with the first-axial-direction-side end of the fin portion at a boundary between the unit main body portion and the first taper tubular portion.

4. The rotary unit according to claim 3,
wherein in the fin portion, the fin diametric dimension at the first-axial-direction-side end of the fin portion is the same as the first projection diametric dimension at the second-axial-direction-side end of the first projecting portion, and the fin diametric dimension at the first reference position is maximum.

5. The rotary unit according to claim 1, further comprising:
a second taper tubular portion which is provided on the second axial direction side with respect to the unit main body portion, a second-axial-direction-side end of the second taper tubular portion forming a second-axial-direction-side end of the rotary unit, a first-direction-side end of the second taper tubular portion being contiguous with the second-axial-direction-side end of the unit main body portion, an outer diameter of the second taper tubular portion becoming smaller toward the second axial direction; and
a second projecting portion which is extended on an outer peripheral portion of the second taper tubular portion between the second-axial-direction-side end of the rotary unit and the first-axial-direction-side end of the second taper tubular portion in a state projecting toward the outer peripheral direction, the second projecting portion being spirally extended around the longitudinal axis, a second projection diametric dimension between the longitudinal axis and a projection projecting end of the second projecting portion becoming larger from the second axial direction toward the first axial direction in the second projecting portion,
wherein a second-axial-direction-side end of the fin portion is located at the second-axial-direction-side end of the unit main body portion or on the first axial direction side with respect to the second-axial-direction-side end of the unit main body portion, and
wherein the fin diametric dimension becomes larger from the second-axial-direction-side end of the fin portion toward a second reference position, the second reference position being located on the first axial direction side with respect to the second-axial-direction-side end of the fin portion and being located on the second axial direction side with respect to the first reference position, a projecting amount of the fin portion from the outer peripheral portion of the unit main body portion becoming larger toward the second reference position in a region between the second-axial-direction-side end of the unit main body portion and the second reference position.

6. The rotary unit according to claim 5,
wherein the second projecting portion is one of a plurality of second projecting portions which are provided between the first-axial-direction-side end of the second taper tubular portion and the second-axial-direction-side end of the second taper tubular portion, the second projecting portions being disposed away from one another in the directions around the longitudinal axis.

7. The rotary unit according to claim 5,
wherein a first-axial-direction-side end of the second projecting portion is contiguous with the second-axial-direction-side end of the fin portion at a boundary between the unit main body portion and the second taper tubular portion.

8. The rotary unit according to claim 7,
wherein in the fin portion, the fin diametric dimension at the second-axial-direction-side end of the fin portion is the same as the second projection diametric dimension at the first-axial-direction-side end of the second projecting portion, and the fin diametric dimension at the second reference position is maximum, and
wherein the fin diametric dimension of the fin portion between the first reference position and the second reference position is constant and maximum.

9. An insertion device comprising:
the rotary unit according to claim 1; and
the inserting section comprising the base section, the rotary unit being attached to the base section and being rotatable with respect to the inserting section in the directions around the longitudinal axis, the rotary unit being positioned on an outer peripheral direction side of the insertion section.

10. The insertion device according to claim 9,
wherein at the first-axial-direction-side end of the rotary unit, an inner diameter of the first taper tubular portion is the same as an outer diameter of the inserting section, and the outer diameter of the first taper tubular portion is at a ratio of 1 to 1.26 with respect to the outer diameter of the inserting section, and
wherein at the first-axial-direction-side end of the rotary unit, an acute angle between the outer peripheral portion of the first taper tubular portion and an outer peripheral portion of the inserting section is from 5° to 20°.

11. The insertion device according to claim 9,
wherein the rotary unit comprises:
a second taper tubular portion which is provided on the second axial direction side with respect to the unit main body portion, a second-axial-direction-side end of the second taper tubular portion forming a second-axial-direction-side end of the rotary unit, a first-direction-side end of the second taper tubular portion being contiguous with the second-axial-direction-side end of the unit main body portion, an outer diameter of the second taper tubular portion becoming smaller toward the second axial direction; and
a second projecting portion which is extended on an outer peripheral portion of the second taper tubular portion between the second-axial-direction-side end of the rotary unit and the first-axial-direction-side end of the second taper tubular portion in a state projecting toward the outer peripheral direction, the second projecting portion being spirally extended around the longitudinal axis, a second projection diametric dimension between the longitudinal axis and a projection projecting end of the second projecting portion becoming larger from the second axial direction toward the first axial direction in the second projecting portion.

12. The insertion device according to claim 11,
wherein at the second-axial-direction-side end of the rotary unit, an inner diameter of the second taper tubular portion is the same as an outer diameter of the inserting section, and the outer diameter of the second taper tubular portion is at a ratio of 1 to 1.26 with respect to the outer diameter of the inserting section, and wherein at the second-axial-direction-side end of the rotary unit, an acute angle between the outer peripheral portion of the second taper tubular portion and an outer peripheral portion of the inserting section is from 5° to 20°.

13. The insertion device according to claim 9, further comprising:

a drive unit which is configured to be driven to rotate the rotary unit, the drive unit being configured to rotate the rotary unit toward one of the directions around the longitudinal axis, thereby allowing a propelling force toward the second axial direction to act on the inserting section and the rotary unit, and the drive unit being configured to rotate the rotary unit toward the other of the directions around the longitudinal axis, thereby allowing a propelling force toward the first axial direction to act on the inserting section and the rotary unit.

14. The rotary unit according to claim 1, wherein a boundary between the outer peripheral portion of the first taper tubular portion and the outer peripheral portion of the inserting section is not formed as a stepped portion.

* * * * *